(12) United States Patent
Wisniewski et al.

(10) Patent No.: US 7,632,816 B2
(45) Date of Patent: Dec. 15, 2009

(54) TREATMENT OF ALZHEIMER AMYLOID DEPOSITION

(75) Inventors: Thomas Wisniewski, Staten Island, NY (US); Marcin Sadowski, Bronx, NY (US); Einar M. Sigurdsson, New York, NY (US); Blas Frangione, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/810,919

(22) Filed: Mar. 26, 2004

(65) Prior Publication Data

US 2004/0214774 A1 Oct. 28, 2004

Related U.S. Application Data

(60) Provisional application No. 60/458,986, filed on Mar. 28, 2003.

(51) Int. Cl.
*A61K 38/00* (2006.01)
*A61K 38/04* (2006.01)
*A61K 39/00* (2006.01)
*A01N 37/18* (2006.01)
*C07K 14/00* (2006.01)
*C07K 16/00* (2006.01)

(52) U.S. Cl. .............................. 514/13; 514/2; 530/326; 530/300; 530/332; 424/185.1

(58) Field of Classification Search ........................ None
See application file for complete search history.

(56) References Cited

U.S. PATENT DOCUMENTS 5,187,153 A 2/1993 Cordell et al.
5,948,763 A 9/1999 Soto-Jara et al.

FOREIGN PATENT DOCUMENTS

WO WO 99/27944 * 10/1999

OTHER PUBLICATIONS

FASEB Journal, 1995, vol. 9, No. 5, pp. 366-370.*
Drug Aging, 2002, 19 (7), pp. 487-494.*
Sato et al., 1998, Nature Medicine, 1998, vol. 4, 7, pp. 822-826.*
Bales et al., "Apolipoprotein E is Essential for Amyloid Deposition in the APPV717F Transgenic Mouse Model of Alzheimer's Disease," Proc. Natl. Acad. Sci. (USA) 96:15233-15238 (1999).
Bales et al., "Lack of Apolipoprotein E Dramatically Reduces Amyloid Beta-Peptide Deposition," Nature Gen. 17:263-264 (1997).
Barrow et al., "Solution Conformations and Aggregational Properties of Synthetic Amyloid Beta-Peptides of Alzheimer's Disease. Analysis of Circular Dichroism Spectra," J. Mol. Biol. 225:1075-1093 (1992).
Buttini et al., "Modulation of Alzheimer-Like Synaptic and Cholinergic Deficits in Transgenic Mice by Human Apolipoprotein E Depends on Isoform, Aging and Overexpression of Amyloid Beta Peptides but not on Plaque Formation," J. Neurosci. 22:10539-10548 (2002).
Castano et al., "Fibrillogenesis in Alzheimer's Disease of Amyloid Beta Peptides and Apolipoprotein E," Biochem. J. 306:599-604 (1995).
Demattos et al., "ApoE and Clusterin Cooperatively Suppress ABeta Levels and Deposition: Evidence that ApoE Regulates Extracellular ABeta Metabolism In Vivo," Neuron 41:193-202 (2004).
Golabek et al., "Amyloid Beta Binding Proteins In Vitro and In Normal Human Cerebrospinal Fluid," Neurosci. Lett. 191:79-82 (1995).
Golabek et al., "The Interaction Between Apolipoprotein E and Alzheimer's Amyloid Beta-peptide is Dependent on Beta-Peptide Conformation," J. Biol. Chem. 271:10602-10606 (1996).
Holtzman et al., "Apolipoprotein E Isoform-Dependent Amyloid Deposition and Neuritic Degeneration in a Mouse Model of Alzheimer's Disease," Proc. Natl. Acad. Sci. (USA) 97:2892-2897 (2000).
Holtzman et al., "Expression of Human Apolipoprotein E Reduces Amyloid-Beta Deposition in a Mouse Model of Alzheimer's Disease," J. Clin. Invest. 103:R15-R21 (1999).
Ji et al., "Amyloid Beta40/42 Clearance Across the Blood-Brain Barrier Following Intra-Ventricular Injections in Wild-Type, ApoE Knock-Out and Human ApoE3 or E4 Expressing Transgenic Mice," J. Alz. Dis. 3:23-30 (2001).
Ji et al., "Apolipoprotein E Isoform-Specific Regulation of Dendritic Spine Morphology in Apolipoprotein E Transgenic Mice and Alzheimer's Disease Patients," Neuroscience 122:305-315 (2003).
Ma et al., "Alzheimer ABeta Neurotoxicity: Promotion by Antichymotrypsin, ApoE4; Inhibition by ABeta-Related Peptides," Neurobiol. Aging 17:773-780 (1996).
Ma et al., "Amyloid-Associated Proteins Alpha 1-Antichymotrypsin and Apolipoprotein E Promote Assembly of Alzheimer Beta-protein into Filaments," Nature 372:92-94 (1994).
Naslund et al. "Characterization of Stable Complexes Involving Apolipoprotein E and the Amyloid Beta Peptide in Alzheimer's Disease Brain," Neuron 15:219-228 (1995).
Sadowski et al. "A Synthetic Peptide Blocking the Apolipoprotein E/Beta-Amyloid Binding Mitigates Beta-Amyloid Toxicity and Fibril Formation In Vitro and Reduces Beta-Amyloid Plaques in Transgenic Mice," Am. J. Pathol. 165:937-948 (2004).

(Continued)

*Primary Examiner*—Olga N Chernyshev
(74) *Attorney, Agent, or Firm*—Nixon Peabody LLP

(57) ABSTRACT

The present invention is directed to a method of preventing or treating Alzheimer's Disease or of inhibiting accumulation of amyloid-β deposits in a subject by administering to the subject an agent which inhibits interaction between amyloid-β and proteins which chaperone amyloid-β under conditions effective to prevent or treat Alzheimer's Disease in the subject or to inhibit accumulation of amyloid-β deposits in the subject's brain, respectively. Another embodiment of the present invention relates to a method of inhibiting interaction between apolipoprotein E and amyloid-β by administering an agent which blocks interaction of apolipoprotein E and amyloid-β under conditions effect to block such interaction.

6 Claims, 7 Drawing Sheets

OTHER PUBLICATIONS

Selkoe, "The Origins of Alzheimer Disease: A is for Amyloid," JAMA 283:1615-1617 (2000).

Shuvaev and Siest, "Interaction Between Human Amphipathic Apolipoproteins and Amyloid Beta-peptide: Surface Plasmon Resonance Studies," FEBS Lett. 383:9-12 (1996).

Sigurdsson et al., "Immunization with a Nontoxic/Nonfibrillar Amyloid-Beta Homologous Peptide Reduces Alzheimer's Disease Associated Pathology in Transgenic Mice," Am. J. Pathol. 159:439-447 (2001).

Sigurdsson et al., "In vivo Reversal of Amyloid Beta Lesions in Rat Brain," J. Neuropath. Exp. Neurol. 59:11-17 (2000).

Soto et al., "Alzheimer's Beta-Amyloid Peptide is Conformationally Modified by Apolipoprotein E In Vitro," Neuroreport 7:721-725 (1996).

Strittmatter et al., "Apolipoprotein E: High-Avidity Binding to Beta-amyloid and Increased Frequency of Type 4 Allele in Late-onset Familial Alzheimer Disease," Proc. Natl. Acad. Sci. (USA) 90:1977-1981 (1993).

Wisniewski et al., "Acceleration of Alzheimer's Fibril Formation by Apolipoprotein E In Vitro," Am. J. Pathol. 145:1030-1035 (1994).

Wisniewski and Frangione, "Apolipoprotein E: A Pathological Chaperone Protein in Patients with Cerebral and Systemic Amyloid," Neurosci. Lett. 135:235-238 (1992).

Wisniewski et al., "Apolipoprotein E: Binding to Soluble Alzheimer's Beta-Amyloid," Biochem. Biophys. Res. Commun. 192:359-365 (1993).

Wisniewski et al., "Diffuse, Lake-like Amyloid-Beta Deposits in the Parvopyramidal Layer of the Presubiculum in Alzheimer Disease," Journal of Neuropathology & Experimental Neurology 57:674-683 (1998).

Zlokovic "Cerebrovascular Transport of Alzheimer's Amyloid Beta and Apolipoproteins J and E: Possible Anti-Amyloidogenic Role of the Blood-Brain Barrier," Life Sci. 59:1483-1497 (1996).

Zlokovic et al., "Brain Uptake of Circulating Apolipoproteins J and E Complexed to Alzheimer's Amyloid Beta," Biochem. Biophys. Res. Commun. 205:1431-1437 (1994).

Andersen et al., "Do Nonsteroidal Anti-inflammatory Drugs Decrease the Risk for Alzheimer's Disease?" Neurology 45:1441-5 (1995).

Selkoe, "Translating Cell Biology into Therapeutic Advances in Alzheimer's Disease," Nature 399:A23-31 (1999).

* cited by examiner

Figures 1A-B
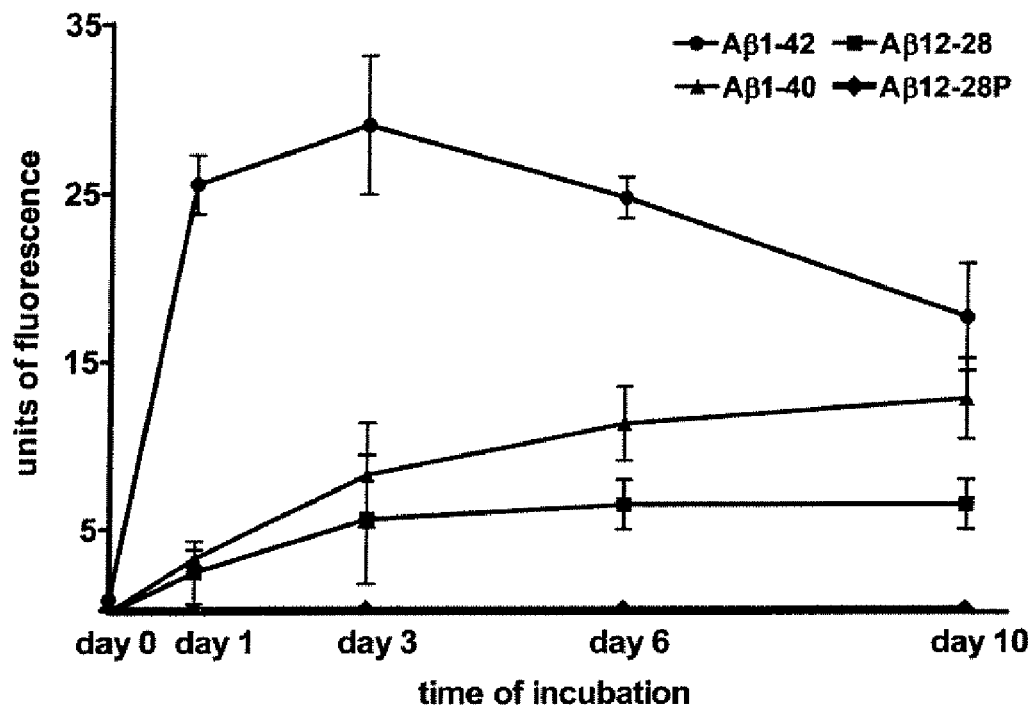
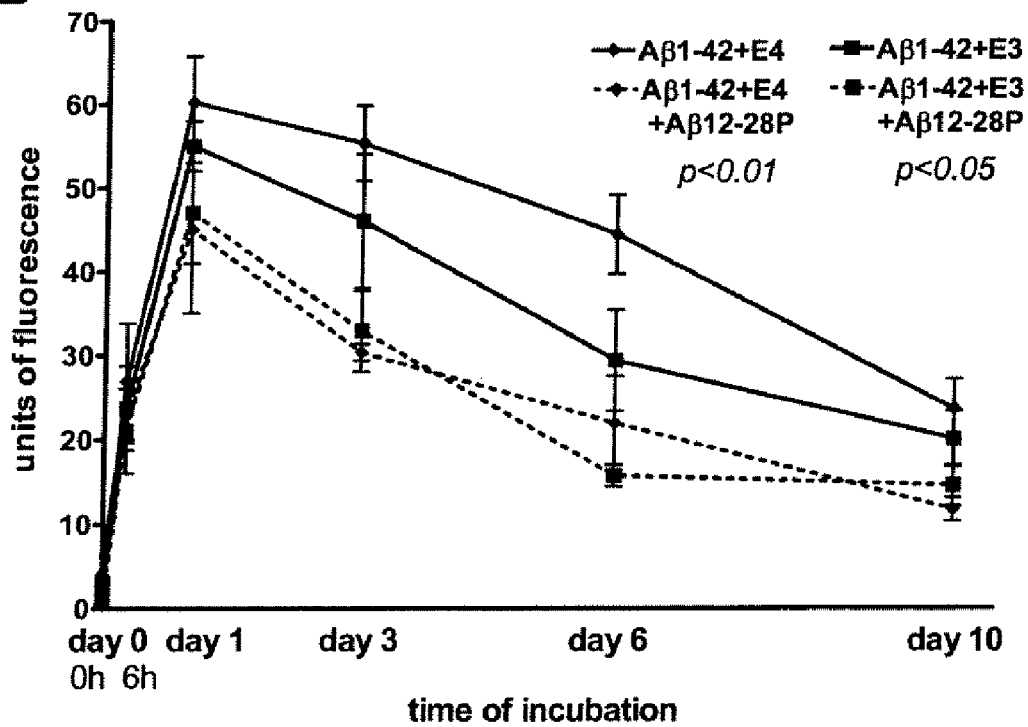

Figures 2A-B
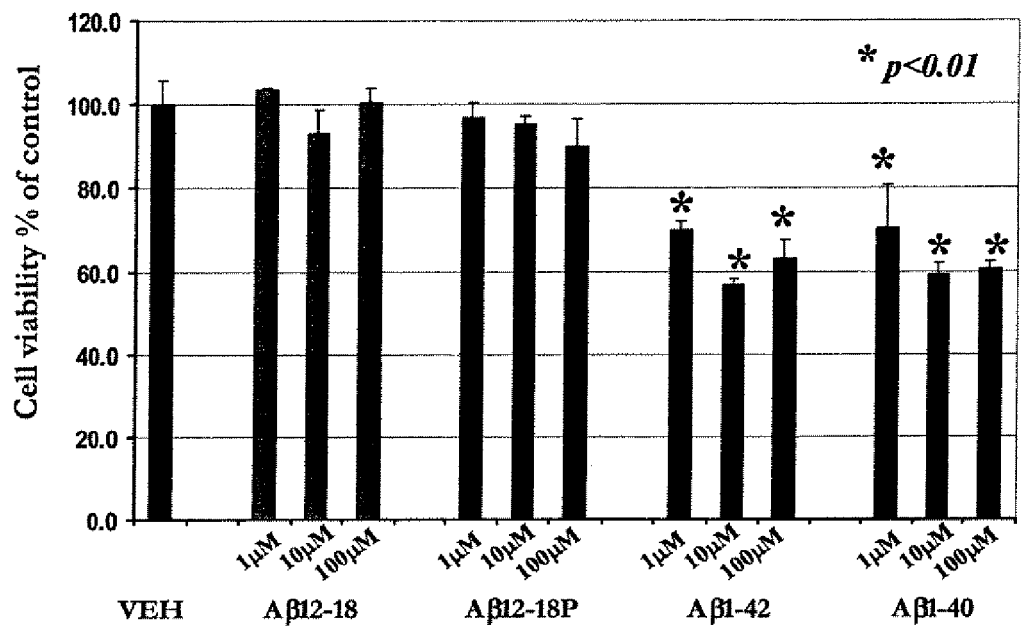
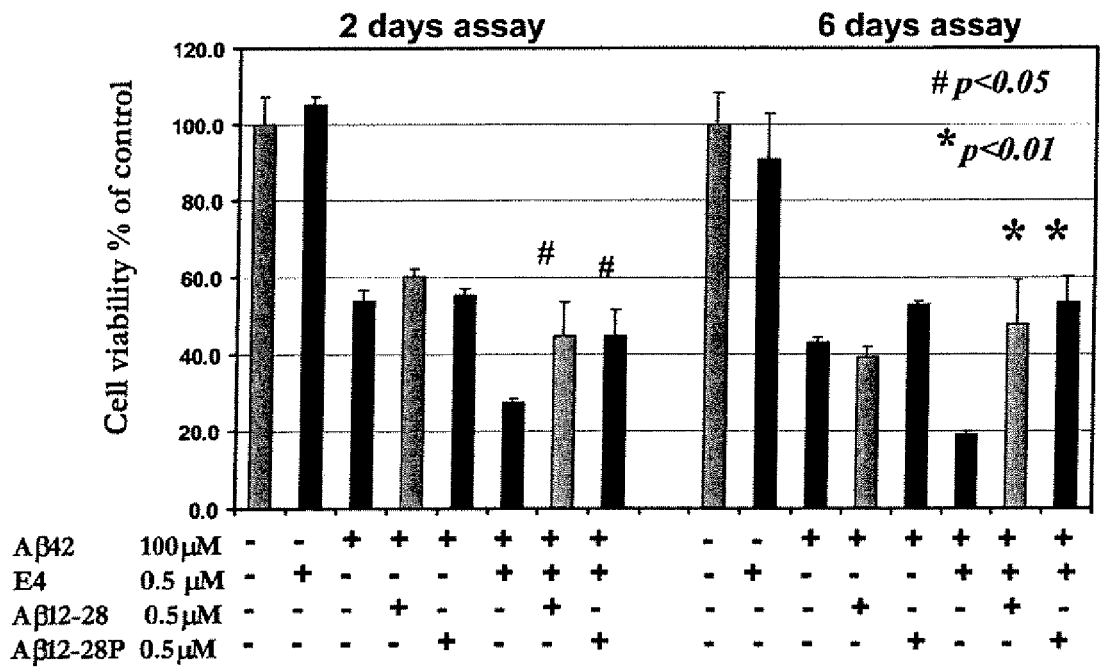

Figures 5A-B
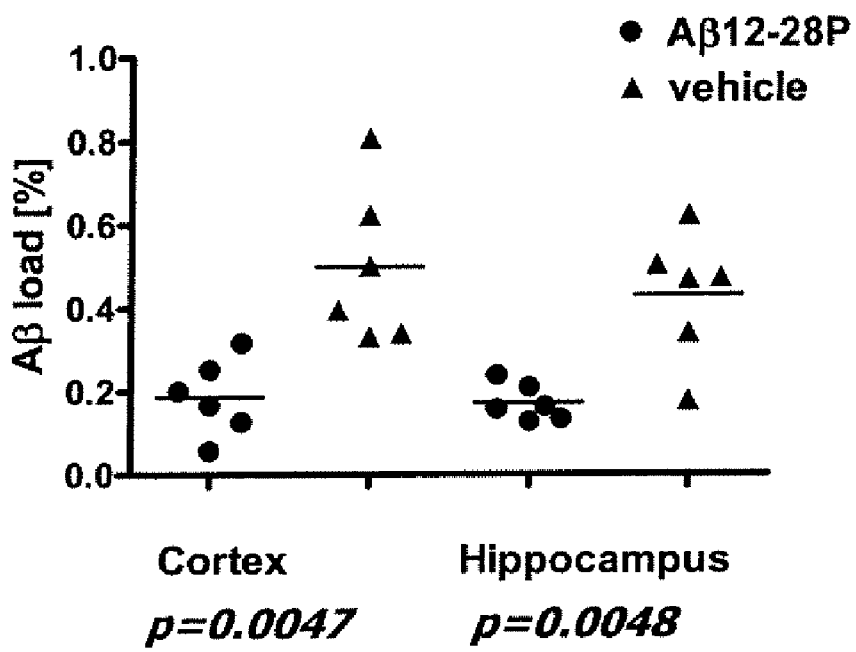
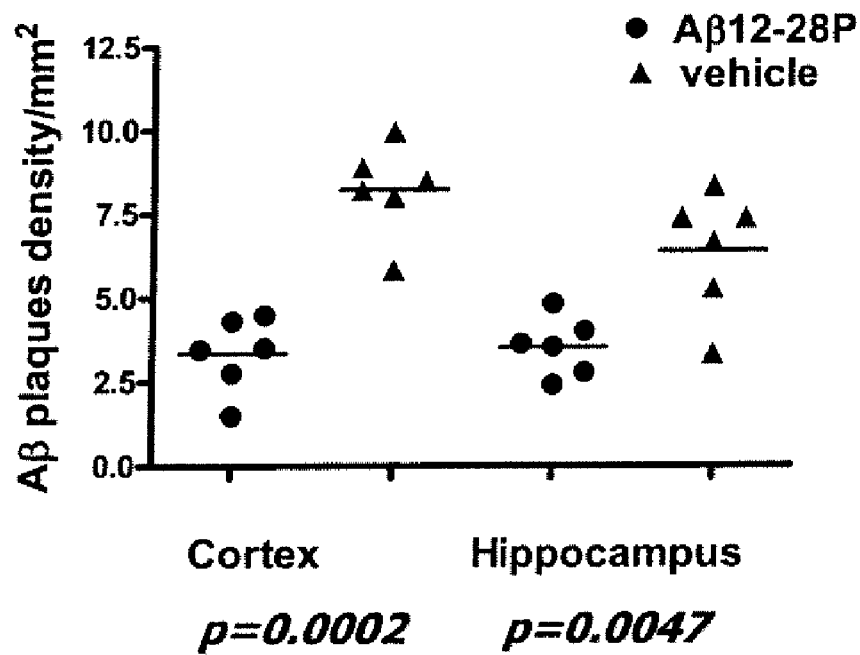

Figures 6A-H
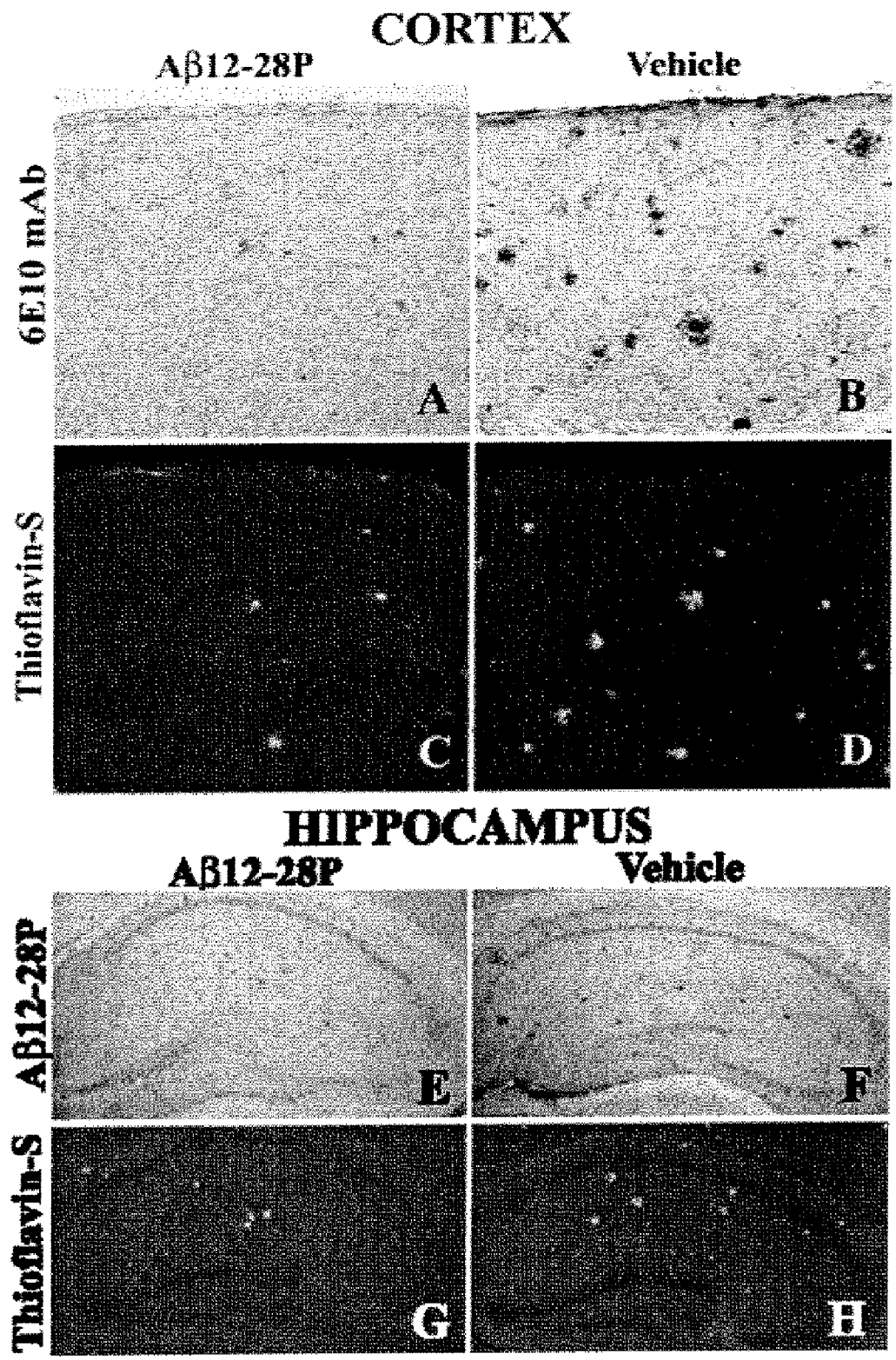

Figures 7A-B
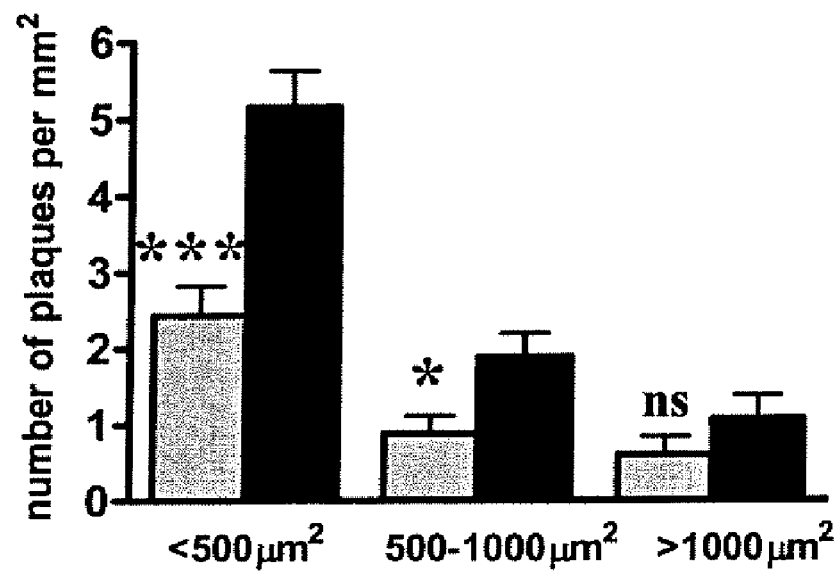
A — CORTEX
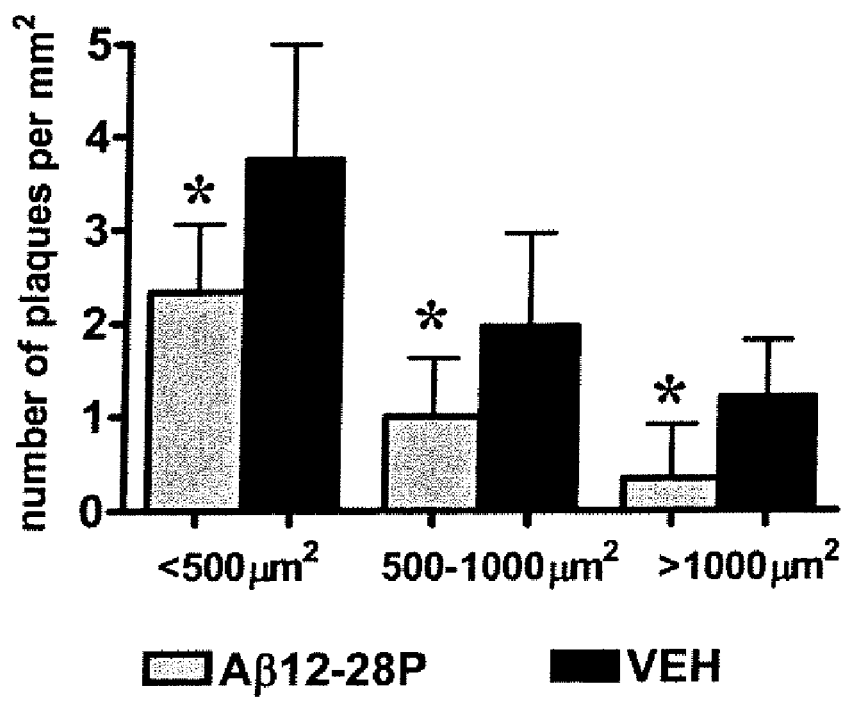
B — HIPPOCAMPUS
☐ Aβ12-28P   ■ VEH

```
                         SEQUENCE LISTING

<160> NUMBER OF SEQ ID NOS: 4

<210> SEQ ID NO 1
<211> LENGTH: 40
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 1

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 43
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 2

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala Ile
        35                  40
```

```
<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 3

Val His His Gln Lys Leu Val Phe Phe Ala Glu Asp Val Gly Ser Asn
  1               5                  10                  15

Lys

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence:  synthetic
      peptide

<400> SEQUENCE: 4

Val His His Gln Lys Leu Pro Phe Phe Ala Glu Asp Val Gly Ser Asn
  1               5                  10                  15

Lys
```

TREATMENT OF ALZHEIMER AMYLOID DEPOSITION

This application claims the benefit of U.S. Provisional Patent Application Ser. No. 60/458,986, filed Mar. 28, 2003, which is hereby incorporated by reference in its entirety.

The subject matter of this application was made with support from the United States Government under National Institutes of Health Grant Nos. AG20747 and AG15408. The United States Government may have certain rights.

FIELD OF THE INVENTION

The present invention is directed to a method of preventing and treating Alzheimer's Disease or inhibiting accumulation of amyloid-β deposits in a subject or to a method of inhibiting the interaction between apolipoprotein E and amyloid-β.

BACKGROUND OF THE INVENTION

A disturbance of amyloid-β ("Aβ") homeostasis in Alzheimer's disease ("AD") leads to the accumulation of this peptide in the form of plaques in the brain (Selkoe, "The Origins of Alzheimer Disease: A is for Amyloid," *JAMA* 283:1615-1617 (2000)). Increased production of Aβ peptides or their inadequate clearance can lead to brain accumulation. It has been demonstrated that peptide homologues to Aβ form amyloid fibrils in solution if they reach a critical concentration (Barrow et al., "Solution Conformations and Aggregational Properties of Synthetic Amyloid Beta-Peptides of Alzheimer's Disease. Analysis of Circular Dichroism Spectra," *J. Mol. Biol.* 225:1075-1093 (1992)). This process can be effectively promoted by pathological chaperone proteins such as apolipoprotein E ("apoE"), especially its E4 isoform (Wisniewski et al., "Acceleration of Alzheimer's Fibril Formation by Apolipoprotein E in vitro," *Am. J. Pathol.* 145:1030-1035 (1994)), ∝1-antichymotrypsin ("ACT") (Ma et al., "Amyloid-associated Proteins Alpha 1-Antichymotrypsin and Apolipoprotein E Promote Assembly of Alzheimer Beta-protein into Filaments," *Nature* 372:92-94 (1994)), or C1q complement factor (Johnson et al., "The Alzheimer's A Beta-peptide is Deposited at Sites of Complement Activation in Pathologic Deposits Associated with Aging and Age-related Macular Degeneration," *Proc. Natl. Acad. Sci. (USA)* 99:11830-11835 (2002)). They promote formation of Aβ fibrils, which remain sequestered within the brain and accumulate in the form of plaques (Castano et al., "Fibrillogenesis in Alzheimer's Disease of Amyloid Beta Peptides and Apolipoprotein E," *Biochem. J.* 306:599-604 (1995)). Inheritance of the apoE4 isoform has been identified as a major genetic risk factor for sporadic, late-onset AD (Schmechel et al., "Increased Amyloid Beta-peptide Deposition in Cerebral Cortex as a Consequence of Apolipoprotein E Genotype in Late-onset Alzheimer Disease," *Proc. Natl. Acad. Sci. (USA)* 90:9649-9653 (1993)) and correlates with an earlier age of onset and greater Aβ deposition in an allele-dose-dependent manner (Schmechel et al., "Increased Amyloid Beta-peptide Deposition in Cerebral Cortex as a Consequence of Apolipoprotein E Genotype in Late-onset Alzheimer Disease," *Proc. Natl. Acad. Sci. (USA)* 90:9649-9653 (1993); Rebeck et al., "Apolipoprotein E in Sporadic Alzheimer's Disease: Allelic Variation and Receptor Interactions," *Neuron* 11:575-580 (1993)). ApoE is a 34-kDa glycosylated protein existing in three major isoforms: E2, E3, and E4, which differ in primary sequence at two residues. In vitro, all apoE isoforms can propagate the β-sheet content of Aβ peptides promoting fibril formation, with apoE4 being the most efficient (Wisniewski et al., "Acceleration of Alzheimer's Fibril Formation by Apolipoprotein E in vitro," *Am. J. Pathol.* 145:1030-1035 (1994); Ma et al., "Amyloid-associated Proteins Alpha 1-Antichymotrypsin and Apolipoprotein E Promote Assembly of Alzheimer Beta-protein into Filaments," *Nature* 372:92-94 (1994); Golabek et al., "The Interaction Between Apolipoprotein E and Alzheimer's Amyloid β-peptide is Dependent on β-peptide Conformation," *J. Biol. Chem.* 271:10602-10606 (1996)). The importance of apoE to Aβ deposition has also been confirmed in vivo. Crossing $APP^{V717F}$ AD transgenic ("Tg") mice onto an apoE knock out ("KO") background, resulted in a substantial reduction of the Aβ load and absence of fibrillar Aβ deposits (Bales et al., "Lack of Apolipoprotein E Dramatically Reduces Amyloid β-peptide Deposition," *Nature Gen.* 17:263-264 (1997)).

Approaches under development for treatment of AD focus on (1) inhibition of enzymes responsible for Aβ cleavage (i.e. Aβ secretases), (2) vaccination, and (3) β-sheet breakers (i.e. compound inhibiting Aβ fibrillogenesis by directly binding to Aβ) (Permanne et al., "Reduction of Amyloid Load and Cerebral Damage in a Transgenic Mouse Model of Alzheimer's Disease by Treatment With a β-sheet Breaker Peptide," *FASEB Journal* (2002)). Currently, no treatment targeting the pathomechanism of AD and halting progression of the disease is available.

The present invention is directed to overcoming the deficiencies in existing methods of treating AD.

SUMMARY OF THE INVENTION

The present invention is directed to a method of preventing or treating Alzheimer's Disease in a subject by administering to the subject an agent which inhibits interaction between amyloid-β and proteins which chaperone amyloid-β under conditions effective to prevent or treat Alzheimer's Disease in the subject.

Another embodiment of the present invention relates a method of inhibiting accumulation of amyloid-β deposits in a subject's brain by administering to the subject an agent which inhibits interaction between amyloid-β and proteins which chaperone amyloid-β under conditions effective to inhibit accumulation of amyloid-β deposits in the subject's brain.

A further embodiment of the present invention relates to a method of inhibiting interaction between apolipoprotein E and amyloid-β by administering an agent which blocks interaction of apolipoprotein E and amyloid-β under conditions effect to block such interaction.

One can speculate that selective ablation of the apoE effect on Aβ could potentially have a therapeutic effect leading to reduced Aβ deposition. ApoE hydrophobically binds to Aβ forming SDS insoluble complexes (Strittmatter et al., "Apolipoprotein E: High-avidity Binding to Beta-amyloid and Increased Frequency of Type 4 Allele in Late-onset Familial Alzheimer Disease," *Proc. Natl. Acad. Sci. (USA)* 90:1977-1981 (1993); Wisniewski et al., "Apolipoprotein E: Binding to Soluble Alzheimer's Beta-amyloid," *Biochem. Biophys. Res. Commun.* 192:359-365 (1993); Naslund et al. "Characterization of Stable Complexes Involving Apolipoprotein E and the Amyloid Beta Peptide in Alzheimer's Disease Brain," *Neuron* 15:219-228 (1995); which are hereby incorporated by reference in their entirety). Although the affinity of binding depends on Aβ conformation (Aβ soluble vs. fibrillar), the binding remains in the low nanomolar range (Golabek et al., "The Interaction Between Apolipoprotein E and Alzheimer's Amyloid β-peptide is Dependent on β-peptide Conformation," *J. Biol. Chem.* 271:10602-10606 (1996); Strittmatter et al., "Apolipoprotein E: High-avidity Binding to Beta-amyloid and Increased Frequency of Type 4 Allele in Late-onset Familial Alzheimer Disease," *Proc. Natl. Acad. Sci.* (*USA*) 90:1977-1981 (1993); Golabek et al., "Amyloid β Binding Proteins in vitro and In Normal Human Cerebrospinal Fluid," *Neurosci. Lett.* 191:79-82 (1995); Shuvaev et al., "Interaction Between Human Amphipathic Apolipoproteins and Amyloid β-peptide: Surface Plasmon Resonance Studies," *REBS Lett.* 383:9-12 (1996); which are hereby incorporated by reference in their entirety). Prior studies identified residues 12-28 of Aβ as the binding site for apoE binding on Aβ (Golabek et al., "The Interaction Between Apolipoprotein E and Alzheimer's Amyloid β-peptide is Dependent on β-peptide Conformation," *J. Biol. Chem.* 271:10602-10606 (1996); Strittmatter et al., "Apolipoprotein E: High-avidity Binding to Beta-amyloid and Increased Frequency of Type 4 Allele in Late-onset Familial Alzheimer Disease," *Proc. Natl. Acad. Sci.* (*USA*) 90:1977-1981 (1993); Ma et al., "Alzheimer Aβ Neurotoxicity: Promotion by Antichymotrypsin, ApoE4; Inhibition by Aβ-related Peptides," *Neurobiol. Aging* 17:773-780 (1996); which are hereby incorporated by reference in their entirety). Hence, synthetic peptide homologues to residues 12-28 of Aβ can be used as competitive agonists of the binding of full length Aβ to apoE. However, Aβ12-28 is known to be fibrillogenic and can be associated with toxicity (Gorevic et al., "Ten to Fourteen Residue Peptides of Alzheimer's Disease Protein are Sufficient for Amyloid Fibril Formation and its Characteristic S-ray Diffraction Pattern," *Biochem. Biophys. Res. Commun.* 147:854-862 (1987), which is hereby incorporated by reference in its entirety). Therefore, the Aβ12-28 sequence has been modified by substitution of the valine at residue 18 to proline, rendering this peptide non-fibrillogenic and non-toxic. Substitutions of valine at residue 18 can also be with other amino acids which render the peptide non-toxic. Further modifications include using D-amino acids, amidation of the C-terminus, and acetylation of the N-terminus in order to extend the serum half-life of the peptide. In a series of experiments, the effect of pharmacological blockade of apoE's pathological chaperoning properties on Aβ fibrillogenesis and toxicity was examined in vitro using Aβ12-28 and Aβ12-28P. Aβ12-28P was also administered to AD Tg mice to investigate the in vivo effect of blocking the apoE/Aβ interaction on amyloid deposition.

Here, it is demonstrated that blocking the specific binding site for Aβ on ApoE, formation of Aβ deposits in the brain of transgenic animals is inhibited. This approach appears to be nontoxic, because it does not inhibit any physiological reaction (like blocking Aβ secretases which serve multiple functions) and does not cause an autoimmune response (like the vaccine whose phase II clinical trial was stopped due to morbidity and mortality) (Sigurdsson et al., "Immunization for Alzheimer's Disease," *Drug Development Research* 56:135-142 (2002), which is hereby incorporated by reference in its entirety).

BRIEF DESCRIPTION OF THE DRAWINGS

FIG. 1A is a graph of a Thioflavin-T assay which demonstrates the modest ability of Aβ12-28 to form fibrils which is significantly lower than Aβ1-40 and Aβ1-42 ($p<0.0001$, repeated measures ANOVA; Aβ12-28 vs. Aβ1-40 and Aβ12-28 vs. Aβ1-42 $p<0.001$ Tukey HSD post-hoc test). No fibrils were formed by Aβ12-28P. FIG. 1B is a graph showing Aβ1-42 incubated in the presence of either apoE3 or apoE4 (solid lines). The chaperoning effect of apoE3 and apoE4 on Aβ1-42 fibril formation was significantly reduced when apoE was preincubated with equimolar concentrations of Aβ12-28P ($p<0.001$, repeated measures ANOVA; $p<0.01$ and $p<0.05$ Tukey HSD post-hoc test for specific effect of Aβ12-28P on ApoE4 and apoE3, respectively).

FIGS. 2A-B are graphs of a cytotoxicity assay using SK-N-SH human neuroblastoma cells. FIG. 2A demonstrates that no significant reduction in viability was observed when cells were incubated with Aβ12-28 or Aβ12-28P. In contrast, even the lowest concentration of Aβ1-40 or Aβ1-42, resulted in a significant cytotoxic effect (one-way ANOVA $p<0.0001$, post-hoc Dunnett's test $p<0.01$ vs. control) VEH-vehicle. FIG. 2B shows that toxicity of Aβ1-42 in cell culture was increased in the presence of apoE4 ($p<0.01$ Aβ1-42 vs. Aβ1-42/apo E4). This effect of apoE could be neutralized if apoE4 was pre-incubated with Aβ12-28 or Aβ12-28P (Aβ1-42/apoE4 vs. Aβ1-42/apoE4/Aβ12-28 or Aβ1-42/apoE4/Aβ12-28P, $p<0.05$, for two-day assay and $p<0.01$ for 6-day assay). ApoE alone did not reduce cell viability. A slightly increased cell viability was observed if Aβ1-42 was incubated with Aβ12-28P without apoE for six days ($p<0.05$), but not for two days. Adding Aβ12-28 to Aβ1-42 did not produced significant improvement in cell viability. For clarity of FIGS. 2A-B, only significance between Aβ1-42/apoE4 vs. Aβ1-42/apoE4/Aβ12-28 and Aβ1-42/apoE4/Aβ12-28P, were marked.

FIGS. 5A-B are graphs showing a significant reduction in the area covered by Aβ (Aβ load, FIG. 5A) and in the numerical density of Aβ plaques (FIG. 5B) observed in APP$^{K670N/M671L}$/PS1$^{M146L}$ Tg mice treated with Aβ12-28P compared to age-matched Tg control animals treated with placebo, and calculated using unbiased stereology by an investigator blinded to the experimental status of the animals.

FIGS. 6A-H are photographs showing lower Aβ load in the cortex and in the hippocampus as observed in APP$^{K670N/M671L}$/PS1$^{M146L}$ Tg ice (A,C,E,G) following four weeks of treatment with Aβ12-28P, compared to age matched double Tg mice in which development of β-amyloidosis was unaltered (B,D,F,H). In treated animals, reduction in both components of Aβ load (numerical density and cross-section area of plaques) were noticed on sections stained with 6E10 mAb (A,B,E,F) and Thioflavin-S (C,D,G,H), which detects only fibrillar Aβ deposits. Scale bar A-D 125 µm, E-H 500 µm.

FIGS. 7A-B are graphs showing that treatment with Aβ12-28P resulted in reduced number of small (<500 µm$^2$), medium-sized (>500-<1000 µm$^2$) and large plaques (>1000 µm$^2$) both in the cortex (FIG. 7A) and in the hippocampus (FIG. 7B). This suggests that inhibition of the Aβ/apoE interaction has an effect on the development of new plaques, as well as the rate of deposition of Aβ on existing plaques. *$p<0.05$, $p<0.01$, *$p<0.001$, one-tailed unpaired t-test.

DETAILED DESCRIPTION OF THE INVENTION

Figure 3:
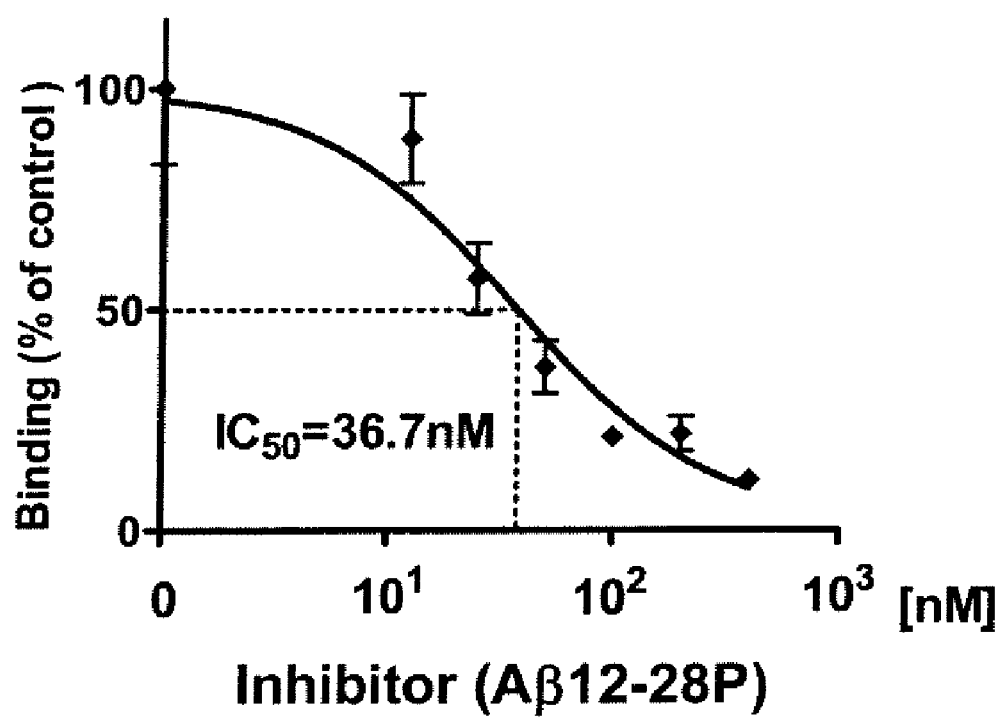
FIG. 3 is a graph showing the results of a competitive inhibition assay in which Aβ12-28P (0-400 nM/L) was pre-incubated with 100 nmol/L apoE4 and added to Aβ1-40 coated wells. Results are expressed as a percentage of residual apoE4 binding, assuming binding of apoE4 in the absence of inhibitor as 100%. Data represents the mean±standard deviation of three independent duplicate experiments fitted into one-site competition curve. Half of maximal inhibition ($IC_{50}$) was calculated to be 36.7 nM.

The present invention is directed to a method of preventing or treating Alzheimer's Disease in a subject by administering to the subject an agent which inhibits interaction between amyloid-β and proteins which chaperone amyloid-β under conditions effective to prevent or treat Alzheimer's Disease in the subject.

Another embodiment of the present invention relates a method of inhibiting accumulation of amyloid-β deposits in a subject's brain by administering to the subject an agent which inhibits interaction between amyloid-β and proteins which chaperone amyloid-β under conditions effective to inhibit accumulation of amyloid-β deposits in the subject's brain.

A further embodiment of the present invention relates to a method of inhibiting interaction between apolipoprotein E and amyloid-β by administering an agent which blocks interaction of apolipoprotein E and amyloid-β under conditions effect to block such interaction.

Examples of the protein which chaperones amyloid-β include α-chymotrypsin and apolipoprotein E.

In one embodiment of the present invention, the agent used to carry out the above methods can be in the form of a protein or a peptidomimetic. Examples of suitable proteins are the proteins having the amino acid sequences of SEQ ID NOs: 2 or 3.

Alternatively, a non-proteinaceous agent can be used to practice the methods of the present invention. Such an agent can have a three dimensional structure like that of the proteins comprising the amino acid sequence of SEQ ID NOs: 2 or 3.

In a further alternative, the agent is a protein comprising an amino acid sequence of at least 5 of the amino acids, in sequence, of SEQ ID NOs: 3 or 4.

A further embodiment of the present invention involves the use of proteins comprising the amino acid sequence of SEQ ID NOs: 3 or 4, where the protein is prepared with D-amino acids, an amidated C-terminus, or an acetylated N-terminus.

To the extent a protein is used to carry out the methods of the present invention, it can be made by well known recombinant techniques.

The nucleic acid molecule encoding the peptide of the present invention can be introduced into an expression system or vector of choice using conventional recombinant technology. Generally, this involves inserting the nucleic acid molecule into an expression system to which the molecule is heterologous (i.e., not normally present). The heterologous nucleic acid molecule is inserted into the expression system or vector in proper sense (5'→3') orientation and correct reading frame. The vector contains the necessary elements for the transcription and translation of the inserted protein-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK± or KS± (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the protein-encoding sequence of the present invention. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The nucleic acid molecule(s) of the present invention, a promoter molecule of choice, a suitable 3' regulatory region, and if desired, a reporter gene, are incorporated into a vector-expression system of choice to prepare the nucleic acid construct of present invention using standard cloning procedures known in the art, such as described by Sambrook et al., *Molecular Cloning: A Laboratory Manual*, Third Edition, Cold Spring Harbor: Cold Spring Harbor Laboratory Press, N.Y. (2001), which is hereby incorporated by reference in its entirety.

The nucleic acid molecule encoding a protein of choice is inserted into a vector in the sense (i.e., 5'→3') direction, such that the open reading frame is properly oriented for the expression of the encoded protein under the control of a promoter of choice. Single or multiple nucleic acids may be ligated into an appropriate vector in this way, under the control of a suitable promoter, to prepare a nucleic acid construct of the present invention.

Once the isolated nucleic acid molecule encoding the peptide of the present invention has been cloned into an expression system, it is ready to be incorporated into a host cell. Recombinant molecules can be introduced into cells via transformation, particularly transduction, conjugation, lipofection, protoplast fuision, mobilization, particle bombardment, or electroporation. The DNA sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like.

Alternatively, proteins in accordance with the present invention can be synthesized from individual amino acids. In particular, the proteins may be synthesized from monomeric amino acids through condensation reactions that form peptide bonds. The proteins are constructed sequentially by coupling the C-terminus of a monomeric amino acid with the N-terminus of the growing peptide. To prevent unwanted reactions involving the amino groups and carboxyl groups of the side chains during the coupling steps, a protecting (i.e., blocking) group is attached to the side chains. In the last steps of synthesis, the side chain-protecting groups are removed and the peptide is cleaved from the resin on which synthesis occurs.

A typical task in the design and synthesis of peptides is to identify a linear sequence of amino acid residues exhibiting a desired biological activity, e.g., binding affinity to a target molecule. In the simplest case, there are only two parameters subject to optimization: (i) the number of sequence positions (peptide length), and (ii) the type of residue present at each sequence position.

The typical experimental approach to peptide design is to perform large-scale random screening which has become feasible due to recent advances in peptide synthesis and activity detection techniques (Gausepohl et al., "Automated Multiple Peptide Synthesis," *Pept. Res.* 5:315-320 (1992); Kramer and Schneider-Mergener, "Synthesis and Screening of Peptide Libraries on Cellulose Membrane Supports," *Methods Mol. Biol.* 87:25-39 (1998); Kramer et al., "Molecular Basis for the Binding Promiscuity of an Anti-p24 (HIV-1) Monoclonal Antibody," *Cell* 91:799-809 (1997); which are hereby incorporated by reference in their entirety). Blind screening is essential if no information about function determining residue patterns is available. This is particularly true when conventional structure-based molecule modeling cannot be performed due to the lack of high-resolution receptor structures. If however, a template peptide or other information is already known that can be used to limit the search space, it is worthwhile following some kind of rational design (Schneider et al., "Peptide Design by Artificial Neural Networks and Computer-based Evolutionary Search," *Proc. Natl. Acad. Sci.* (*USA*) 95:12179-12184 (1998); Schneider and Wrede, "The Rational Design of Amino Acid Sequences by Artificial Neural Networks and Simulated Molecular Evolution: De novo Design of an Idealized Leader Peptidase Cleavage Site," *Biophys. J.* 66:335-344 (1994); Huang et al., "Development of a Common 3D Pharmacophore for Delta-opioid Recognition from Peptides and Non-peptides Using a Novel Computer Program," *J. Comput. Aided Mol. Des.* 11:21-28 (1997); Mee et al., "Design of Active Analogues of a 15-residue Peptide Using D-optimal Design, QSAR and a Combinatorial Search Algorithm," *J. Pept. Res.* 49:89-102 (1997); which are hereby incorporated by reference in their entirety).

In practicing the method of the present invention, the administering step is carried out by administering the agent of the present invention orally, intradermally, intramuscularly, intraperitoneally, intravenously, subcutaneously, or intranasally. The agent of the present invention may be administered alone or with suitable pharmaceutical carriers, and can be in solid or liquid form, such as tablets, capsules, powders, solutions, suspensions, or emulsions.

The agent of the present invention may be orally administered, for example, with an inert diluent, or with an assimilable edible carrier, or it may be enclosed in hard or soft shell capsules, or it may be compressed into tablets, or they may be incorporated directly with the food of the diet. For oral therapeutic administration, the agent of the present invention may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of the agent of the present invention in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The agent of the present invention may also be administered parenterally. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agent of the present invention may also be administered directly to the airways in the form of an aerosol. For use as aerosols, the agent of the present invention in solution or suspension may be packaged in a pressurized aerosol container together with suitable propellants, for example, hydrocarbon propellants like propane, butane, or isobutane with conventional adjuvants. The agent of the present invention also may be administered in a non-pressurized form such as in a nebulizer or atormizer.

EXAMPLES

Example 1

Synthetic Peptides and Proteins

The following synthetic peptides were used in this study: Aβ1-40, which has an amino acid sequence corresponding to SEQ ID NO: 1 as follows:
DAEFRHDSGYEVHHQKLVFFAEDVGSNK-
GAIIGLMVGGVV Aβ1-42, which has an amino acid sequence corresponding to SEQ ID NO: 2 as follows:
DAEFRHDSGYEVHHQKLVFFAEDVGSNK-
GAIIGLMVGGVVIAI Aβ12-28, which has an amino acid sequence corresponding to SEQ ID NO: 3 as follows:
VHHQKLVFFAEDVGSNK Aβ12-28P, which has an amino acid sequence corresponding to SEQ ID NO: 4 as follows:
VHHQKLPFFAEDVGSNK In order to minimize degradation by endogenous peptidases and extend the half-life, Aβ12-28P (and Aβ12-28 as a control) were synthesized using D-amino acids and were end protected by amidation of the C-terminus and acetylation of the N-terminus. Aβ12-28P and Aβ12-28 used for all in vitro and in vivo experiments originated from the same batch of large scale peptide synthesis. Details of synthesis, purification, and sequence verification were described previously (Sigurdsson et al., "In vivo Reversal of Amyloid β Lesions in Rat Brain," *J. Neuropath. Exp. Neurol.* 59:11-17 (2000); Sigurdsson et al., "Immunization with a Nontoxic/Nonfibrillar Amyloid-β Homologous Peptide Reduces Alzheimer's Disease Associated Pathology in Transgenic Mice," *Am. J. Pathol.* 159:439-447 (2001); Matsubara et al., "Apolipoprotein J and Alzheimer's Amyloid β Solubility," *Biochem. J.* 316:671-679 (1996); which are hereby incorporated by reference in their entirety). For aggregation studies and assessment of secondary structure, the peptides were initially diluted in 1,1,1,3,3,3-hexafluoro-2-propanol (HFIP; Sigma, St. Louis, Mo.) at a concentration of 10 mM/ml, aliquoted and lyophilized. HFIP treatment renders peptides monomeric with minimal β-sheet content (Stine et al., "In vitro Characterization of Conditions for Amyloid-beta Peptide Oligomerization and Fibrillogenesis," *J. Biol. Chem.* 278:11612-11622 (2003), which is hereby incorporated by reference in its entirety). Lyophilized peptides were stored at −80° C. and resuspended immediately prior to each experiment in the appropriate diluent. For in vivo experiments, a 1 mg/ml stock solution of Aβ12-28P was prepared in 50% acetonitrile containing 0.1% trifluoroacetic acid which was aliquoted, lyophilized, and stored at −80° C. until use.

Recombinant apoE3 and apoE4 were purchased from Calbiochem Corp. (San Diego, Calif.). Lipidated apoE3 and apoE4 complexes were prepared from primary cultures of astrocytes derived from Tg mice in which human apoE3 or apoE4 were expressed under the control of the astrocyte-specific glial fibrillary acidic protein (GFAP) promoter as described previously (Fagan et al., "Unique Lipoproteins Secreted by Primary Astrocytes from Wild Type, ApoE (−/−), and Human ApoE Transgenic Mice," *J. Biol. Chem.* 274: 30001-30007 (1999); DeMattos et al., "Purification and Characterization of Astrocyte-secreted Apolipoprotein E and J-Containing Lipoproteins from Wild-type and Human ApoE Transgenic Mice," *Neurochemistry International* 39:415-425 (2001); Sun et al., "Glial Fibrillary Acidic Protein-apolipoprotein E (apoE) Transgenic Mice: Astrocyte-specific Expression and Differing Biological Effects of Astrocyte-secreted ApoE3 and ApoE4 Lipoproteins," *J. Neurosci.* 18:3261-3272 (1998); which are hereby incorporated by reference in their entirety). Briefly, primary cultures of forebrain astrocytes were maintained in serum-free Dulbecco's modified Eagle's medium/Ham's F-12 (1:1), with N2 supplement (Invitrogen, Carlsbad, Calif.) for 72 hours. The medium was removed and clarified by centrifugation at 800×g for 5 minutes and then concentrated by ultrafiltration. Human apoE was isolated by immunoaffinity chromatography. The purity of the apoE preparation was assessed by SDS-PAGE. The lipidated apoE3 and apoE4 prepared by this method were in the form of HDL-like lipoprotein particles 8, 11, and 14 nm in diameter as assessed by non-denaturating gradient gel electrophoresis (NDGGE) (DeMattos et al., "Purification and Characterization of Astrocyte-secreted Apolipoprotein E and J-containing Lipoproteins from Wild-type and Human ApoE Transgenic Mice," *Neurochemistry International* 39:415-425 (2001), which is hereby incorporated by reference in its entirety).

Example 2

Circular Dichroism Studies of Secondary Structure

Circular dichroism ("CD") was used to study the secondary structure of peptides in solution as described previously (Golabek et al., "The Interaction Between Apolipoprotein E and Alzheimer's Amyloid β-peptide is Dependent on β-peptide Conformation," *J. Biol. Chem.* 271:10602-10606 (1996); Soto et al., "Alzheimer's Soluble β-amyloid is Conformationally Modified by Apolipoproteins in vitro," *Neuroreport* 7:721-725 (1996); which are hereby incorporated by reference in their entirety). Aliquots of HFIP treated peptides were diluted in 5 mmol/L Tris buffer (pH 7.0) to obtain a peptide concentration of 100 μmol/L, and were incubated at 37° C. CD was measured at indicated intervals with t=0 being immediately after the peptide was reconstituted. Measurements were on a Jasco J-720 spectropolarimeter (Easton, Md.), equipped with a model CTC-344 circular temperature control system (Neslab Inc., Newington, N.H.), at final protein concentration of 0.15 mg/ml in a cell with 0.1 cm path length. The spectra were recorded at 1 nm intervals over the wavelength range of 190-260 nm at 15° C. Results were expressed as molar ellipticity in units of deg-cm$^2$-dmol$^{-1}$, and the data were analyzed by the Lincomb, convex constraints and neural network algorithms to obtain percentages of different types of secondary structures using Softsec software (Softwood Inc., PA.) (Perczel et al., "Analysis of Circular Dichroism Spectrum of Proteins Using the Convex Constraint Algorithm," *Anal. Biochem.* 203:83-93 (1992); Manavalan et al., "Variable Selection Method Improves the Prediction of Protein Secondary Structure from Circular Dichroism," *Anal. Biochem.* 167:76-85 (1987); Toumadje et al., "Extending CD Spectra of Proteins to 168nm Improves the Analysis for Secondary Structures," *Anal. Biochem.* 200:321-331 (1992); Sreerma et al., "A Self-consistent Method for the Analysis of Protein Secondary Structure from Circular Dichroism," *Anal. Biochem.* 209:32-44 (1993); which are hereby incorporated by reference in their entirety).

Example 3

Aggregation and Fluorometric Experiments

The fibrillogenic potential of Aβ12-28 and Aβ12-28P was investigated using a Thioflavin-T assay according to previously published methods (Wisniewski et al., "Acceleration of Alzheimer's Fibril Formation by Apolipoprotein E in vitro," *Am. J. Pathol.* 145:1030-1035 (1994); Castano et al., "Fibrillogenesis in Alzheimer's Disease of Amyloid Beta Peptides and Apolipoprotein E," *Biochem. J.* 306:599-604 (1995); which are hereby incorporated by reference in their entirety). Aβ1-40 and Aβ1-42 were studied for comparison. Aβ12-28 and Aβ12-28P used for these experiments were both synthesized from D-amino acids to avoid effect of different racemic conformers on the fibril formation. All peptides were HFIP treated and reconstituted in 100 mM Tris buffer (pH 7.4) to obtain a 100 μmol/L concentration. Aβ1-40 or Aβ1-42 (100 μmol/L) were also incubated in the presence of 1 μmol/L of apoE3 or E4. In aggregation, inhibition experiments, apoE3 or E4 were preincubated with Aβ12-28 or Aβ12-28P in a ratio 1:2 for 6 h at 37° C. and then added to instantly reconstituted Aβ1-40 or Aβ1-42. Peptides were incubated over a period of 10 days at 37° C. Samples containing 15 μg of incubated peptides were taken at indicated intervals and fluorescence was measured as previously described in a Perkin-Elmer LS-50B fluorescence spectrophotometer (Perkin Elmer Instruments, Shelton, Conn.) (Wisniewski et al., "Acceleration of Alzheimer's Fibril Formation by Apolipoprotein E in vitro," *Am. J. Pathol.* 145:1030-1035 (1994); Golabek et al., "The Interaction Between Apolipoprotein E and Alzheimer's Amyloid β-peptide is Dependent on β-peptide Conformation," *J. Biol. Chem.* 271:10602-10606 (1996); which are hereby incorporated by reference in their entirety). The mean±standard deviation ("SD") for three separate experiments was plotted in FIG. 1. Differences in amount of fibrils formed by the different peptides were evaluated by means of a repeated measures ANOVA, followed by a Tukey HSD post-hoc test using Statistica (version 6.1) (StatSoft Inc., Tulsa, Okla.).

Example 4

Cell Culture Neurotoxicity Studies

The effect of 1-100 μmol/L concentrations of Aβ12-28 and Aβ12-28P on the viability of the SK-N-SH human neuroblastoma cell line (American Type Culture Collection, Manassas, Va.) was compared to the well established neurotoxicity of Aβ1-40 and Aβ1-42 in tissue culture (Sigurdsson et al., "Immunization with a Nontoxic/Nonfibrillar Amyloid-β Homologous Peptide Reduces Alzheimer's Disease Associated Pathology in Transgenic Mice," *Am. J. Pathol.* 159:439-447 (2001), which is hereby incorporated by reference in its entirety). SK-N-SH cells were plated at 10,000 cells/100 μl per well in flat-bottom, 96-well microtiter plates and incubated with 1-100 μmol/L concentrations of tested peptides for two days after which cell viability was assessed using a metabolic assay, which is based on cleavage of the yellow tetrazolium salt (MTT) to purple formazan crystals by viable cells. The MTT assay (Roche Molecular Biochemicals, Indianapolis, Ind.) was performed according to the manufacturer's instructions.

In toxicity rescue experiments, Aβ12-28 or Aβ12-28P were used to neutralize apoE4's effect on Aβ1-42 neurotoxicity. Aβ12-28 or Aβ12-28P were preincubated with apoE4 in an equimolar concentration for 6 h at 37° C., then mixed with Aβ1-42, followed by addition to microtiter plates containing cells prepared as described above. The obtained results were compared to the viability of cells incubated with Aβ1-42 alone and Aβ1-42 with apoE4. Cells incubated with apoE alone, Aβ1-42+Aβ12-28 and Aβ1-42+Aβ12-28P, were used as additional controls. The final concentration of peptides was as follows: Aβ1-42 100 μmol/L, Aβ12-28 and Aβ12-28P 0.5 μmol/L, and apoE4 0.5 μmol/L. Two- and six-day experiments were performed and cell viability was assessed using the MTT assay. All experiments were run in triplicate. The results from cell culture neurotoxicity studies were evaluated by one-way analysis of variance, followed by a Dunnett's test as a post hoc analysis.

Example 5

Competitive Inhibition Assay

Inhibition of Aβ1-40 binding to apoE4 in the presence of Aβ12-28P was analyzed by enzyme-linked immunosorbent assay (ELISA) (Matsubara et al., "Characterization of Apolipoprotein J-Alzheimer's A Beta Interaction," *J. Biol. Chem.* 270:7563-7567 (1995), which is hereby incorporated by reference in its entirety). Polystyrene microtiter plates (Immulon-2) (Dynatech Lab., Chantilly, Va.) were coated overnight with Aβ1-40 (400 ng/well/100 µL), washed and blocked with Superblock (Pierce, Rockford, Ill.). Under these conditions, 10 ng/well of Aβ1-40 was bound to the well as determined by a modification of Quantigold assay (Diversified Biotech., Boston, Mass.) (Matsubara et al., "Characterization of Apolipoprotein J-Alzheimer's A Beta Interaction," *J. Biol. Chem.* 270:7563-7567 (1995), which is hereby incorporated by reference in its entirety). Lipidated apoE4 100 nM was preincubated with an increasing concentration of Aβ12-28P (0-400 nM) in 10 mM Tris buffer pH 7.4 for three hours at 37° C., and then added to the plate (100 µL/well). After another three hours of incubation, at the same temperature, the plate was washed, and apoE4 bound to Aβ1-42 was detected using 3D12 mAb 1:1000 (Biodesign Int., Saco, Mass.), followed by incubation with anti-mouse IgG HRP-conjugate (Amersham, Piscataway, N.J.) at 1:5000. The color reaction was developed with a 3,3,5,5-tetramethybenzidine substrate (Sigma, St. Louis, Mo.), stopped with 2M sulfuric acid, and optical density ("OD") was read at 450 nm on a 7520 Microplate Reader (Cambridge Technology, Watertown, Mass.). Non-specific binding was determined using bovine serum albumin and/or omitting the apoE4 in the assay. OD values were converted to percentages with the binding of apoE4 in the absence of inhibitor being considered as 100%. The mean±standard deviation from three independent duplicate experiments was plotted in FIG. 3 and analyzed by a one site competition nonlinear regression fit algorithm using GraphPad Prism v4.0 (GraphPad Software, San Diego, Calif.).

Example 6

The Blood-Brain-Permeability Studies

Aβ1-40 was labeled with Na[$^{125}$I] (Amersham Bioscience, Piscataway, N.J.) using IODO-BEADS® (Pierce, Rockford, Ill.) according to the manufacturer's instructions. Unbound $^{125}$I was removed using a gel filtration column (Bio-Gel P-6) (Bio-Rad, Hercules, Calif.) (Haugland et al., "Preparation of Avidin Conjugates," *The Protein Protocols Handbook.* Edited by Walker J M. Humana Press, pp. 365-374, 2002, which is hereby incorporated by reference in its entirety). Because Aβ12-28P does not have tyrosine residues, radiolabeling sites were added by coupling sulfo-succinimidyl-4-hydroxybenzoate (Sulfo-SHB) (Pierce, Rockford, Ill.) to side chain amino groups of lysine residues (Aβ positions 16 and 28) (Bolton et al., "Labeling of Proteins to High Specific Radioactivities by Conjugation to A I-125-containing Acylating Agent—Application to Radiomimmunoassay," *Biochem. J.* 133:529-538 (1973), which is hereby incorporated by reference in its entirety). Aβ12-18P (1 mmol/L) was incubated with 5 mmol/L sulfo-SHB in 0.1 mol PBS (pH 7.2) for 15 min at room temperature (Vaidyanathan et al., "Radioiodination of Proteins Using N-Succinimidyl 4-Hydroxy-3-Iodobenzoate," *Bioconjugate Chem.* 4:78-84 (1993), which is hereby incorporated by reference in its entirety). Excess of sulfo-SHB was removed by overnight dialysis against PBS using a Spectra/Por®CE cellulose ester membrane (molecular weight cut off of 1 kDa) (Spectrum Laboratories, Rancho Dominguez, Calif.). Coupling Aβ12-28P with $^{125}$I was performed similarly to radiolabeling of Aβ1-40. The specific activity of radioiodinated peptides was as follows: Aβ12-28P $1.25\times10^8$ cpm/mg and Aβ1-40 $3.77\times10^8$ cpm/mg.

The blood-brain-permeability of Aβ12-28P was assessed using the perfusion and capillary depletion techniques (Zlokovic et al., "Brain Uptake of Circulating Apolipoproteins J and E Complexed to Alzheimer's Amyloid Beta," *Biochem. Biophys. Res. Commun.* 205:1431-1437 (1994); Zlokovic et al., "Blood-brain Barrier Transport of Circulating Alzheimer's Amyloid Beta," *Biochem. Biophys. Res. Commun.* 197:1034-1040 (1993); which are hereby incorporated by reference in their entirety) in 10 C57BLJ wild type mice (22-25 g body weight). When anesthetized by intra-peritoneal injection of Ketamine HCl (0.12 mg/g) and Xylazine (0.016 mg/g) (Yi et al., "Amyloid β40/42 Clearance Across the Blood-brain Barrier Following Intra-ventricular Injections in Wild-type, ApoE Knock-out and Human ApoE3 or E4 Expressing Transgenic Mice," *J. Alz. Dis.* 3:23-30 (2001), which is hereby incorporated by reference in its entirety), the large neck vessels were exposed. The right common carotid artery was cannulated with PE10 polyethylene tubing (Warner Instrument Corp., Hamden, Conn.) connected to a Harvard Apparatus slow-drive syringe pump, and the ipsilateral side of the brain was perfused at a rate of 0.2 ml/min for 10 min. The right jugular vein was cannulated to facilitate sample collection whereas the left jugular vein was cut to allow free flow of excess fluid. Animals were perfused with $^{125}$I-Aβ12-28P (12.3 nmol) or $^{125}$I-Aβ1-40 (11.6 nmol) and inulin [C$^{14}$]-carboxylic acid (1.33 µCi/mg) as a cerebrovascular space marker (molecular weight=5175 Da) (Zlokovic et al., "Brain Uptake of Circulating Apolipoproteins J and E Complexed to Alzheimer's Amyloid Beta," *Biochem. Biophys. Res. Commun.* 205:1431-1437 (1994); Zlokovic et al., "Blood-brain Barrier Transport of Circulating Alzheimer's Amyloid Beta," *Biochem. Biophys. Res. Commun.* 197:1034-1040 (1993); Mackic et al., "Transport Across the Blood-brain Barrier and Differential Cerebrovascular Sequestration of Circulating Alzheimer's Amyloid-β Peptide in Aged Rhesus Versus Aged Squirrel Monkeys," *Vascul. Pharmacol.* 38:303-313 (2002); which are hereby incorporated by reference in their entirety) diluted in perfusion medium containing washed sheep red blood cells suspended at a hematocrit of 20% in saline medium supplemented with 70,000 MW dextran to achieve a physiologic osmotic pressure. The perfusion medium was saturated with a mixture of 96% $O_2$-4% $CO_2$, warmed at 37° C., and filtered through polymer wool before entering the animal's circulation. Under these conditions, the perfusion medium has been shown to maintain a p$CO_2$ of 38-40 mmHg and a pH of 7.35. During perfusion, the concentration of test-tracers in the arterial flow remained constant. After the infusion was completed the brain vasculature was washed out with 20 ml of medium without radiolabeled tracers and the animals were sacrificed by decapitation. The brain was instantly removed from the skull, arachnoid membranes were peeled away and the choroid plexuses were separated by dissection. The ipsilateral hemisphere was homogenized in PBS (1:10 w/v) with a cocktail of protease inhibitors (Complete, Boehringer Mannheim, Mannheim, Germany) and depleted of remaining microvasculature by filtrating the homogenate through mesh nylon net with 60 µm pores. The $^{125}$I and $^{14}$C radioactivity in the brain and vessel fractions were determined in a Beckman 4000 gamma counter and a Beckman LS-7000 liquid scintillation spectrometer, respectively (Beckman-Coulter, Fullerton, Calif.).

Brain uptake of radiolabeled Aβ12-28P and Aβ1-40 was expressed as perfusion ratio (Mackic et al., "Transport Across the Blood-brain Barrier and Differential Cerebrovascular Sequestration of Circulating Alzheimer's Amyloid-β Peptide in Aged Rhesus Versus Aged Squirrel Monkeys," *Vascul. Pharmacol.* 38:303-313 (2002); Permanne et al., "Reduction of Amyloid Load and Cerebral Damage in a Transgenic Mouse Model of Alzheimer's Disease by Treatment with a β-sheet Breaker Peptide," *FASEB J.* 16:860-862 (2002); which are hereby incorporated by reference in their entirety) $V_D = C_{BR}/C_{PL}$, where $C_{BR}$ and $C_{PL}$ are cpm/g of brain and cpm/μl of serum, respectively. The volume of distribution for a given peptide was corrected for capillary uptake by subtracting $V_D$ of inulin from $V_D$ of peptide. $V_D$ of inulin was on average 14±5 μl/g.

Example 7

Determination of the Half-Life of Aβ12-28P

The half life of Aβ12-28P was determined after a single bolus injection of 80 μg end-protected $^{125}$I-Aβ12-28P (dissolved in 0.5 cc of sterile PBS) into a femoral vein of six anesthetized wild type C57BL6 mice. Blood samples were collected at given time points. Serum was separated from plasma by centrifugation at 10,000×g for 10 minutes. The trichloroacetic (TCA) acid precipitation method was used to assess the amount of radiolabeled peptide present in the serum (Yi et al., "Amyloid β40/42 Clearance Across the Blood-brain Barrier Following Intra-ventricular Injections in Wild-type, apoE Knock-out and Human apoE3 or E4 Expressing Transgenic Mice," *J. Alz. Dis.* 3:23-30 (2001); Mackic et al., "Transport Across the Blood-brain Barrier and Differential Cerebrovascular Sequestration of Circulating Alzheimer's Amyloid-β Peptide in Aged Rhesus Versus Aged Squirrel Monkeys," *Vascul. Pharmacol.* 38:303-313 (2002); which are hereby incorporated by reference in their entirety). A 30% stock solution of bovine albumin (Sigma, St. Louis, Mo.) in PBS was added to serum samples to obtain a final albumin solution of 5%, which was thoroughly mixed. Serum samples were then precipitated with TCA (final concentration of TCA was 15%) and centrifugated at 25,000×g in a Beckmann TL-100 Ultracentrifuge. Radioactivity was assessed in the pellet fraction using a Beckman 4000 gamma counter. Serum level of $^{125}$I-Aβ12-28P following intranasal peptide administration was assessed in another six wild type C57BL6J mice. Under ketamine/xylazine anesthesia 80 μg of radiolabeled peptide (in 100 μl of PBS) was administered into the nasal cavity. Ten 10 μl drops were instilled into both nostrils alternatively over five minutes. Serum samples were collected and radioactivity in TCA precipitated pellets was measured as described above. The obtained data was transformed into percentage values compared to serum radioactivity following intravenous injections at t=0 as 100%. The mean±standard deviation from all tested animals was plotted in FIG. 4 and analyzed by a one phase exponential decay nonlinear regression fit algorithm using GraphPad Prism v4.0. To compare the extent of drug bioavailability after the administration of a single intravenous or intranasal dose the area under both curves were calculated (Shargel et al., *Applied Biopharmaceutics and Pharmacokinetics*, McGraw-Hill, 1999, which is hereby incorporated by reference in its entirety).

Example 8

Testing Activity of Aβ12-28P In Vivo

Initial testing of Aβ12-28P toxicity in vivo was performed on five wild type C57BL6 mice which received intraperitoneal ("i.p.") injections of 1 mg of Aβ12-28P diluted in 0.5 mL of sterile PBS three times per week for four weeks. Mice were observed for an additional two weeks and all remained alive and well. Signs of toxicity included change in body weight, physical appearance, measurable clinical signs, unprovoked behavior and response to external stimuli were not noticed. After one month, the animals were sacrificed and samples were taken from the brain, liver, gut, spleen, kidney and heart, for hematoxylin and eosin staining. The effect of Aβ12-28P on Aβ deposition was tested in $APP^{K670N/M671L}/PS1^{M146L}$ double Tg mice (Hsiao et al., "Correlative Memory Deficits, Aβ Elevation and Amyloid Plaques in Transgenic Mice," *Science* 274:99-102 (1996); Duff et al., "Increased Amyloid-β42 (43) in Brains of Mice Expressing Mutant Presenilin 1," *Nature* 383:710-713 (1996); Holcomb et al., "Behavioral Changes in Transgenic Mice Expressing Both Amyloid Precursor Protein and Presenilin-1 Mutations: Lack of Association with Amyloid Deposits," *Behavior Genetics* 29:177-185 (1999); which are hereby incorporated by reference in their entirety). The first administration of Aβ12-28P was begun at four months of age, at which time the $APP^{K670N/M671L}/PS1^{M146L}$ mice already have significant numbers of Aβ lesions (Wengenack et al., "Quantitative Histological Analysis of Amyloid Deposition in Alzheimer's Double Transgenic Mouse Brain," *Neurosci.* 101:939-944 (2000); McGowan et al., "Amyloid Phenotype Characterization of Transgenic Mice Overexpressing Both Mutant Amyloid Precursor Protein and Mutant Presenilin 1 Transgenes," *Neurobiol. Dis.* 6:231-244 (1999), which are hereby incorporated by reference in their entirety). The treatment was continued for four weeks (1 mg i.p. three times per week). Control age-matched $APP^{K670N/M671L}/PS1^{M146L}$ mice received injections with vehicle only. There were six Aβ12-28P treated and six vehicle treated $APP^{K670N/M671L}/PS1^{M146L}$ mice in this study.

Example 9

Histology

Animals were sacrificed a week after the last injection with an overdose of sodium pentobarbital (150 mg/kg i.p.) and transcardially perfused with 20 ml of heparinized 0.1M PBS followed by 4% buffered paraformaldehyde. The brain was dehydrated using increasing concentrations of sucrose in 0.1M PBS, pH 7.4 and sectioned using a freezing microtome (Leica SM2400) (Nussloch, Germany). Serial coronal sections (40 μm thick) were collected in 10 series. Each of the series contained a complete set of cross-sections along the rostro-caudal axis of the brain spaced by 400 μm. Three random selected section series were stained with either 6E10 monoclonal antibody (mAb) raised against residues 1-16 of Aβ (Kim et al., "Production and Characterization of Monoclonal Antibodies Reactive to Synthetic Cerebrovascular Amyloid Peptide," *Neurosci. Res. Comm.* 2:121-130 (1988), which is hereby incorporated by reference in its entirety), Thioflavin-S for fibrillar amyloid deposits (Wisniewski et al., "Diffuse, Lake-like Amyloid-beta Deposits in the Parvopyramidal Layer of the Presubiculum in Alzheimer Disease," *Journal of Neuropathology & Experimental Neurology* 57:674-683 (1998), which is hereby incorporated by reference in its entirety), or cresyl violet. For Aβ immunohistochemistry, endogenous peroxidase activity was quenched in 0.3% $H_2O_2$ for 30 min and incubation with mAb 6E10 at 1:1000 dilution was followed by an anti-mouse IgG biotinylated secondary antibody (1:2000) and avidin-horseradish peroxidase complex (Vectastain MOM kit) (Vector Laboratories, Burlingame, Calif.). Sections were developed using 3,3'-diaminobenzidine kit with nickel ammonium sulfate (Vector Laboratories, Burlingame, Calif.).

Example 10

Quantification of Aβ Deposition

Aβ deposition were quantified on one randomly selected section series which was stained with 6E10 mAb. Aβ deposits were measured in the brain cortex and in the hippocampus using a random, unbiased sampling scheme. Because sections in the series were separated by a 400 μm gap, 14-15 cross-sections through the cortex and 7 cross-sections through the hippocampus were analyzed. The whole cortical and hippocampal profiles as appearing on the coronal plane cross-sections were traced using the Bioquant image analysis system (R&M Biometrics Inc., Nashville, Tenn.). Test areas (320 μm×240 μm) were randomly selected by the computer algorithm based on randomly applied grid (800 μm×800 μm) over the traced contour. This gave on average of 6-8 test areas per cross-section of the cortex and 3-4 areas per cross-section of the hippocampus. Images of the test areas were captured and a threshold optical density was obtained that discriminated staining from background. Objects smaller than 170 $μm^2$ (average cross-sectional area of a hippocampal pyramidal neuron+two standard deviations) (Sigurdsson et al., "Immunization with a Nontoxic/Nonfibrillar Amyloid-O Homologous Peptide Reduces Alzheimer's Disease Associated Pathology in Transgenic Mice," *Am. J. Pathol.* 159:439-447 (2001); Wadghiri et al., "Detection of Alzheimer's Amyloid in Transgenic Mice Using Magnetic Resonance Micro-imaging," *Magn. Reson. Med.* 50:293-302 (2003); which are hereby incorporated by reference in their entirety) were filtered out and the total area occupied by remaining objects and their number per test field was measured. If needed, artifacts such as non-specific meningeal or vascular staining were eliminated manually. The analysis was done by an investigator blinded to the experimental status of the animals. For each analyzed animal, both Aβ load (i.e. percentage of test area occupied by Aβ) and density of Aβ plaques were calculated. Differences between groups were compared by means of one-tailed unpaired t-test.

Example 11

ELISA Assay for the Anti-Aβ Antibody Titer

Plasma of animals treated with Aβ12-28P were tested for the presence of antibodies against Aβ to determine whether the observed treatment effect is associated with an immune response (Sigurdsson et al., "Immunization with a Nontoxic/Nonfibrillar Amyloid-β Homologous Peptide Reduces Alzheimer's Disease Associated Pathology in Transgenic Mice," *Am. J. Pathol.* 159:439-447 (2001), which is hereby incorporated by reference in its entirety). Plasma of animals vaccinated with Aβ homologues peptide, K6Aβ1-30, given with alum as an adjuvant, which is known to induce an immune response against Aβ, were used as a positive control (Sigurdsson et al., "Immunization with a Nontoxic/Nonfibrillar Amyloid-β Homologous Peptide Reduces Alzheimer's Disease Associated Pathology in Transgenic Mice," *Am. J. Pathol.* 159:439-447 (2001), which is hereby incorporated by reference in its entirety). Immunolon-2, 96 well microtiter plates were coated with Aβ1-42 or Aβ1-40 and blocked with Superblock as described above. The collected mouse sera were initially diluted at 1:50 and subsequent five fold dilutions were made. All samples were run in duplicate and incubated overnight at 4° C. The plates were then washed in PBS, followed by incubation with goat anti-mouse Ig HRP-conjugate (Amersham Pharmacia Biotech, Piscataway, N.J.). Development of color reaction and OD measurements were performed as described above.

Example 12

Study of Peptide Secondary Structure

Studies of the secondary structure were performed on peptides monomerized by HFIP, lyophilized, and reconstituted using 5 mmol/L Tris buffer (pH 7.0). The first measurements, performed immediately after reconstitution, showed that the secondary structure of Aβ12-28 and Aβ12-28P is dominated by ∝-helix and random coil, which constitute 41% and 57%, or 39% and 59%, of the total protein structure, respectively. The β-sheet content of both peptides was minimal (2%), in contrast to Aβ1-42, which had a CD spectrum at time=0 consistent with 49% β-sheet content. The secondary structure of Aβ12-28 and Aβ12-28P remained stable during the 72 h of incubation at 37° C., whereas the β-sheet content of Aβ1-42 increased from 49% to 58%.

Example 13

Study of Amyloid Fibril Formation

None of the HFIP treated peptides were fibrillar at time=0 as assessed by Thioflavin-T assay. Aβ12-28 formed a small amount of fibrils following 24 hours incubation which continued to increase until day 6 when fluorescence levels reached a plateau (FIG. 1A). However, compared to Aβ1-40 or Aβ1-42, the amount of fluorescence emitted by the Aβ12-28 solution was significantly lower (p<0.0001, repeated measures ANOVA; Aβ12-28 vs. Aβ1-40 and Aβ12-28 vs. Aβ1-42 p<0.001, followed by Tukey HSD post-hoc testing). This indicated that the fibrillogenic potential of Aβ12-28 is significantly lower than full length Aβ peptides. Aβ12-28P did not form any fibrils after incubation at 37° C. for 10 days.

ApoE3 and apoE4 act as pathological chaperones for full length Aβ (Wisniewski et al., "Acceleration of Alzheimer's Fibril Formation by Apolipoprotein E in vitro," *Am. J. Pathol.* 145:1030-1035 (1994); Ma et al., "Amyloid-associated Proteins Alpha 1-antichymotrypsin and Apolipoprotein E Promote Assembly of Alzheimer Beta-protein into Filaments," *Nature* 372:92-94 (1994); Wisniewski et al., "Apolipoprotein E: A Pathological Chaperone Protein in Patients with Cerebral and Systemic Amyloid," *Neurosci. Lett.* 135:235-238 (1992); which are hereby incorporated by reference in their entirety). In their presence, the amount of fibrils formed by Aβ1-42 over time is significantly increased (FIG. 1B). However, when lapidated, apoE3 or apoE4 were preincubated with an equimolar concentration of Aβ12-28P before addition to the Aβ1-42 solution; a significantly lower amount of fluorescence was recorded over time (p<0.001, repeated measures ANOVA; p<0.01 and p<0.05 Tukey HSD post-hoc test for specific effect of Aβ12-28P on apoE4 and apoE3, respectively). Addition of the same concentration of Aβ12-28P alone did not have any significant effect on Aβ1-42 fibrillogenesis, indicating that Aβ12-28P does not directly effect full length Aβ fibril formation. After 24 h of incubation, a relative reduction in fluorescence by 25.3% was observed for apoE4 and by 14.5% for apoE3, whereas by day six the reductions were 52.3% and 48.3%, respectively. This decreased fluorescence indicates that when pretreated with Aβ12-28P, both apoE3 and apoE4 have a reduced ability to promote the fibril formation of Aβ1-42. The fluorescence of each of the samples was reduced progressively after day 1, due to aggregation and precipitation of the Aβ1-42, as has been noted in prior studies (Sigurdsson et al., "Immunization with a Nontoxic/Nonfibrillar Amyloid-β Homologous Peptide Reduces Alzheimer's Disease Associated Pathology in Transgenic Mice," *Am. J. Pathol.* 159:439-447 (2001), which is hereby incorporated by reference in its entirety).

Example 14

Cell Culture Cytotoxicity Studies

No significant reduction in the viability of SK-N-SH human neuroblastma cells was observed when cells were incubated with Aβ12-28 or Aβ12-28P at a concentration ranging from 1 μmol/L to 100 μmol/L (FIG. 2A). A significantly reduced viability of SK-N-SH cells was noted after a two day incubation with Aβ1-40 or Aβ1-42 starting from concentration as low as 1 μmol/L (p<0.01). In a separate experiment, Aβ1-42 (100 μmol/L) was incubated with apoE4 (0.5 μmol/L), which was associated with a significantly greater reduction in cell viability compared to incubation with Aβ1-42 alone (p<0.01 (FIG. 2B)). If the apoE4 was preincubated with an equimolar concentration of either Aβ12-28 or Aβ12-28P before adding to Aβ1-42, a significant rescue of the cell viability could be demonstrated (p<0.05 for the two day time point and p<0.01 for the 6 day time point). The viability of SK-N-SH cells incubated in the presence of apoE4 alone (0.5 μmol/L) was not reduced compared to the control group (only vehicle added). Slightly increased cell viability was observed if Aβ1-42 (100 μmol/L) was incubated with Aβ12-28P (0.5 μmol/L) without apoE for six days (p<0.05), but not for two days. Much more striking improvement in cell viability could be demonstrated when 10 μmol/L of Aβ1-42 was incubated with 10 μmol/L of either Aβ12-28 or Aβ12-28P. This effect could not be demonstrated for Aβ12-28.

Example 15

Competitive Inhibition Assay

The ability of Aβ12-28P to specifically bind to apoE and block the binding to the full length Aβ peptides was demonstrated with a competitive inhibition assay. ApoE4 preincubated with increasing concentrations of Aβ12-28P showed a decreased affinity toward immobilized Aβ1-40 (FIG. 3). The concentration of Aβ12-28P producing half-maximal inhibition ($IC_{50}$) was calculated from a non-linear regression, one-site competition curve as 36.7 nM. The inhibition constant ($K_I$) of Aβ12-28P was calculated to be 11.37 nmol given the known dissociation constant ($K_D$) of Aβ1-40 binding to apoE is approximately 10 nmol (Golabek et al., "The Interaction Between Apolipoprotein E and Alzheimer's Amyloid β-peptide Deposition," *Nature Gen.* 17:263-264 (1997); Tokuda et al., "Lipidation of Apolipoprotein E Influences its Isoform-specific Interaction with Alzheimer's Amyloid β Peptides," *Biochem. J.* 348:359-365 (2000); which are hereby incorporated by reference in their entirety).

Example 16

Blood-Brain-Barrier Permeability and Pharmacokinetic Studies

The Blood-Brain-Barrier ("BBB") permeability of Aβ12-28P was studied using the brain perfusion and capillary depletion techniques. The volume of distribution ($V_D$) of $^{125}$I-Aβ12-28P after trans-carotid perfusion was calculated to be 65±20 μL/gram of brain tissue (mean±standard deviation) whereas the $V_D$ of $^{125}$I-Aβ1-40, under the same experimental conditions, was 81.3±40 μL/gram (difference not statistically significant). The Aβ1-40 was radiolabeled by directly attaching $^{125}$I to the tyrosine in position 10, whereas Aβ12-28P was radiolabeled via a sulfo-SHB group attached to the side chain of the four lysines. This required modification of Aβ12-28P is likely to have decreased its BBB permeability. Sulfhydryl groups are known to decrease lipophilicity and therefore to decrease penetration through the BBB compared to the intact peptide (Klunk et al., "Imaging Aβ Plaques in Living Transgenic Mice with Multiphoton Microscopy and Methoxy-X04, a Systemically Administered Congo Red Derivative," *J. Neuropathol. Exp. Neurol.* 61:797-805 (2002), which is hereby incorporated by reference in its entirety). More than 90% of $^{125}$I-Aβ12-28P was found in the capillary depleted brain fraction, indicating that the majority of the peptide crossed into the brain parenchyma and was not retained in the vascular compartment.

Figure 4:
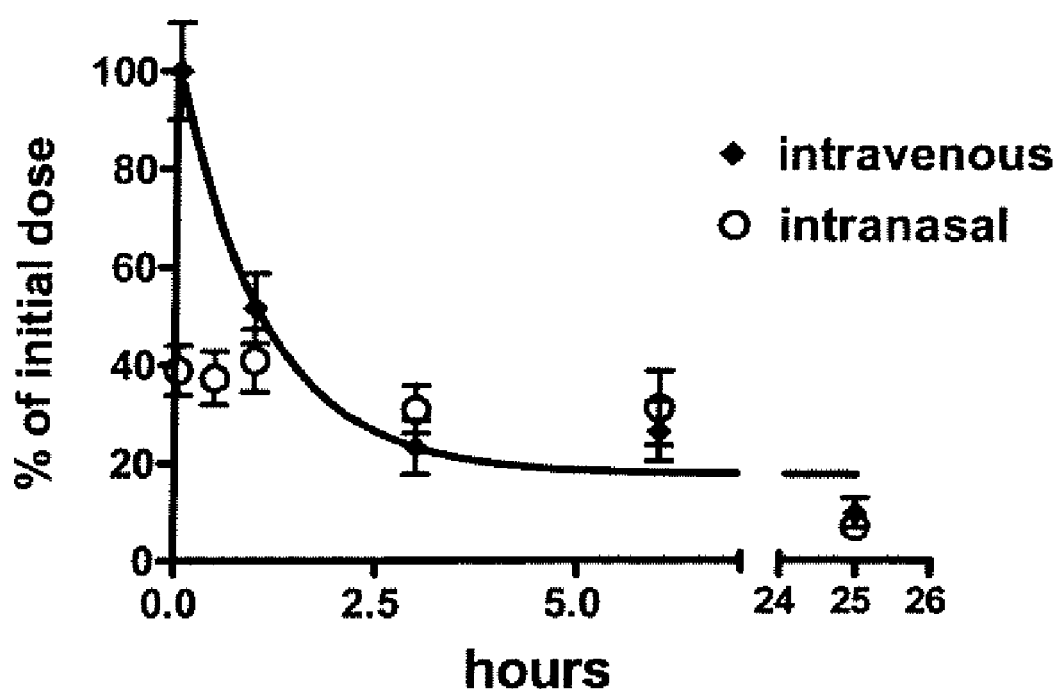
FIG. 4 is a graph which shows serum levels of $^{125}$I-Aβ12-28P following a single intravenous (diamonds) or intranasal (open circles) dose. Values represent the percentage of drug serum level, taking the drug serum level at $t=0$ after intravenous administration as 100%. Values are expressed as a mean±standard deviation for all animals studied (n=6 for intravenous and n=5 for intranasal). The half-life of Aβ12-28P following a single intravenous injection was analyzed using a one phase exponential decay nonlinear regression fit algorithm. It was calculated to be 62.2±18 min.

The plasma half-life of Aβ12-28P was estimated after a single intravenous injection of $^{125}$I-Aβ12-28P to be 62.2±18 min (mean±standard deviation) (FIG. 4). This contrasts with a plasma half life of 2 to 3 minutes for Aβ1-40 (Poduslo et al., "Receptor-mediated Transport of Human Amyloid Beta-protein 1-40 and 1-42 at the Blood-brain Barrier," *Neurobiol. Dis.* 6:190-199 (1999), which is hereby incorporated by reference in its entirety). Calculations used only TCA precipitable counts, as previously reported (Mackic et al., "Transport Across the Blood-brain Barrier and Differential Cerebrovascular Sequestration of Circulating Alzheimer's Amyloid-β Peptide in Aged Rhesus Versus Aged Squirrel Monkeys," *Vascul. Pharmacol.* 38:303-313 (2002); Poduslo et al., "Receptor-mediated Transport of Human Amyloid Beta-protein 1-40 and 1-42 at the Blood-brain Barrier," *Neurobiol. Dis.* 6:190-199 (1999); which are hereby incorporated by reference in their entirety), hence, it is not likely that the analysis is confounded by in vivo hydrolysis of the peptide. The presence of $^{125}$I-Aβ12-28P in the serum could also be demonstrated following intranasal administration. At t=0, the serum level was equal to about 40% of the level achieved after administration of the same amount of peptide intravenously. In contrast to the serum profile, where the level of peptide decreased sharply, following intranasal administration, the serum level remained stable for the first hour and then started to decrease slowly, matching the level of peptide after intravenous administration at t=3 h. However, when the areas under the curve for intravenous and intranasal administration were calculated, no significant differences were found. This indicates that the extent of drug bioavailability after intravenous administration is comparable to bioavailability of the same dose administered intranasally.

Example 17

Reduction of Aβ-Load in APP/PS1 Mice After Aβ12-28P Treatment

Prior to testing the effect of Aβ12-28P on Aβ load in Tg mice, a toxicity test was carried out using five wild type mice which received 1 mg of Aβ12-28P three times a week for four weeks; the same protocol was later used on the Tg mice. No changes were noted in treated animals in terms of body weight, physical appearance, unprovoked behavior, or response to external stimuli. Hematoxylin and eosin stained sections of the brain, heart, liver, gut, spleen, or kidneys did not reveal any pathology.

Treatment with Aβ12-28P was started at the age of four months. After four weeks of peptide administration, the Aβ load in the cortex and in the hippocampus of treated animals was 63.3% p=0.0047) and 61.9% (p=0.0048) lower compared to age-matched control Tg animals, which received vehicle (FIG. 5A, FIG. 6A, FIG. 6B, FIG. 6E, and FIG. 6F). There was also a reduction in the numerical density of Aβ plaques in treated mice by 60.1% in the neocortex (=0.0002) and by 46.3% in the hippocampus p=0.0047) (FIG. 5B). The reduction in the density of Aβ plaques was also seen on Thioflavin-S staining, which selectively labels Aβ deposits in a fibrillar form (FIG. 8C, FIG. 8D, FIG. 8G, and FIG. 8H).

Treatment with Aβ12-28P had a marked effect on reducing the density of plaques in all size categories. There was a 52.8% reduction in the density of small plaques (cross-section area <500 µm$^2$, p<0.001), a 53.5% reduction in the number of medium-size plaques (cross-section area >500 µm$^2$ and <1000 µm$^2$; p<0.05), and a 44% reduction in the number of large plaques (>1000 µm$^2$; non-significant) in the cortex (FIG. 7A). In the hippocampus, the reduction in the density of plaques in each size category was: 37.6% for small plaques (p<0.05), 48.6% for medium-size plaques (p<0.05), and 65.4% for large plaques (p<0.05, FIG. 7B). The decreased number of small plaques in treated Tg mice suggests that the treatment with Aβ12-28P decreases the rate of new plaque formation while the reduced number of medium-size and large plaques suggests a reduced rate of Aβ deposition on existing plaques, limiting plaque growth. This could suggest that treatment with Aβ12-28P would potentially result in both a decreased rate of new plaque formation and decreased growth of existing lesions.

At the time of sacrifice, sera of wild type and Tg mice treated with Aβ12-28P were collected. They were tested for presence of anti-Aβ antibodies. No anti-Aβ antibodies were detected in mice treated with Aβ12-28P, whereas under the same conditions, positive control, sera of APP$^{K670N/M671L}$ mice immunized with K6Aβ1-30-NH$_2$ and alum adjuvant (Sigurdsson et al., "Immunization with a Nontoxic/Nonfibrillar Amyloid-β Homologous Peptide Reduces Alzheimer's Disease Associated Pathology in Transgenic Mice," *Am. J. Pathol.* 159:430-447 (2001), which is hereby incorporated by reference in its entirety) showed the presence of anti-Aβ antibodies with a titer ranging from 1:1000 to 1:10,000. This indicates that the effect of Aβ12-28P on Aβ load cannot be attributed to a humoral response against Aβ.

Accumulation of Aβ, a 39-43 amino acid peptide, in brains of AD patients is a hallmark of AD pathology (Selkoe, "The Origins of Alzheimer Disease: A is for Amyloid," *JAMA* 283:1615-1617 (2000), which is hereby incorporated by reference in its entirety). Complementary pieces of evidences derived from in vivo and in vitro studies have demonstrated that apoE critically promotes Aβ fibrillization and deposition (Wisniewski et al., "Acceleration of Alzheimer's Fibril Formation by Apolipoprotein E in vitro," *Am. J. Pathol.* 145: 1030-1035 (1994); Bales et al., "Lack of Apolipoprotein E Dramatically Reduces Amyloid β-peptide Deposition," *Nature Gen.* 17:263-264 (1997); Ma et al., "Alzheimer Aβ3 Neurotoxicity: Promotion by Antichymotrypsin, ApoE4; Inhibition by Aβ-related Peptides," *Neurobiol. Aging* 17:773-780 (1996); Bales et al., "Apolipoprotein E is Essential for Amyloid Deposition in the APPV717F Transgenic Mouse Model of Alzheimer's Disease," *Proc. Natl. Acad. Sci.* (*USA*) 96:15233-15238 (1999); Holtzman et al., "Apolipoprotein E Isoform-dependent Amyloid Deposition and Neuritic Degeneration in a Mouse Model of Alzheimer's Disease," *Proc. Natl. Acad. Sci.* (*USA*) 97:2892-2897 (2000), which are hereby incorporated by reference in their entirety). The most striking example, emphasizing role of apoE as a pathological chaperone of β-amyloidosis, comes from experiments with generation of APP$^{V717F}$/apoE$^{-/-}$ mice which have a delayed onset of Aβ deposition, a reduced Aβ load, and no fibrillar Aβ deposits, compared to APP$^{V717F}$/apoE$^{+/+}$ Tg mice. APP$^{V717F}$/apoE$^{+/-}$ mice demonstrate an intermediate level of pathology (Bales et al., "Lack of Apolipoprotein E Dramatically Reduces Amyloid β-peptide Deposition," *Nature Gen.* 17:263-264 (1997); Bales et al., "Apolipoprotein E is Essential for Amyloid Deposition in the APPV717F Transgenic Mouse Model of Alzheimer's Disease," *Proc. Natl. Acad. Sci.* (*USA*) 96:15233-15238 (1999); Holtzman et al., "Expression of Human Apolipoprotein E Reduces Amyloid-beta Deposition in a Mouse Model of Alzheimer's Disease," *J. Clin. Invest.* 103:R15-R21 (1999); Holtzman et al., "Apolipoprotein E Isoform-dependent Amyloid Deposition and Neuritic Degeneration in a Mouse Model of Alzheimer's Disease," *Proc. Natl. Acad. Sci.* (*USA*) 97:2892-2897 (2000), which are hereby incorporated by reference in their entirety). Neutralization of the chaperoning effect apoE would therefore potentially have a mitigating effect on Aβ accumulation; however, evidence also suggests that apoE has a role in the clearance of Aβ peptides (Rebeck et al., "Multiple, Diverse Senile Plaque-associated Proteins are Ligands of an Apolipoprotein E Receptor, the Alpha 2-Macroglobulin Receptor/Low-density-lipoprotein Receptor-related Protein," *Ann. Neurol.* 37:211-217 (1995); LaDu et al., "Apolipoprotein E Receptors Mediate the Effects of β-amyloid on Astrocyte Cultures," *J. Biol. Chem.* 275:33974-33980 (2000); Ji et al., "Amyloid β40/42 Clearance Across the Blood-brain Barrier Following Intra-ventricular Injections in Wild-type, ApoE Knock-out and Human apoE3 or E4 Expressing Transgenic Mice," *J. Alz. Dis.* 3:23-30 (2001); DeMattos et al., "ApoE and Clusterin Cooperatively Suppress Aβ Levels and Deposition. Evidence that apoE Regulates Extracellular Aβ Metabolism in vivo," *Neuron* 41:193-202 (2004); which are hereby incorporated by reference in their entirety), as well as other important functions for neuronal maintenance (Nathan et al., "Differential Effects of Apolipoproteins E3 and E4 on Neuronal Growth in vitro," *Science* 264:850-852 (1994); Ji et al., "Apolipoprotein E4 Potentiates Amyloid β Peptide-induced Lysosomal Leakage and Apoptosis in Neuronal Cells," *J. Biol. Chem.* 277: 21821-21828 (2002); Buttini et al., "Modulation of Alzheimer-like Synaptic and Cholinergic Deficits in Transgenic Mice by Human Apolipoprotein E Depends on Isoform, Aging and Overexpression of Amyloid β Peptides but not on Plaque Formation," *J. Neurosci.* 22:10539-10548 (2002); Teter et al., "Role of Apolipoprotein E and Estrogen in Mossy Fiber Sprouting in Hippocampal Slice Cultures," *Neuroscience* 91:1009-1016 (1999); Ji et al., "Apolipoprotein E Isoform-specific Regulation of Dendritic Spine Morphology in Apolipoprotein E Transgenic Mice and Alzheimer's Disease Patients," *Neurosci.* 122:305-315 (2003); which are hereby incorporated by reference in their entirety), therefore it is difficult to predict a priori the in vivo effect of inhibiting the apoE/Aβ interaction. In order to investigate this possible therapeutic mechanism, a peptide homologous to residues 12-28 of Aβ was synthesized, which is the apoE binding domain (Golabek et al., "The Interaction Between Apolipoprotein E and Alzheimer's Amyloid β-peptide is Dependent on β-peptide Conformation," *J. Biol. Chem.* 271:10602-10606 (1996); Strittmatter et al., "Apolipoprotein E: High-Avidity Binding to Beta-amyloid and Increased Frequency of Type 4 Allele in Late-onset Familial Alzheimer Disease," *Proc. Natl. Acad. Sci. (USA)* 90:1977-1981 (1993); Ma et al., "Alzheimer Aβ Neurotoxicity: Promotion by Antichymotrypsin, ApoE4; Inhibition by Aβ-related Peptides," *Neurobiol. Aging* 17:773-780 (1996); which are hereby incorporated by reference in their entirety). Such peptide can act as a competitive inhibitor of the apoE/full length Aβ interaction. To avoid the intrinsic toxicity associated with a residual capacity to form fibrils (Gorevic et al., "Ten to Fourteen Residue Peptides of Alzheimer's Disease Protein are Sufficient for Amyloid Fibril Formation and its Characteristic s-ray Diffraction Pattern," *Biochem. Biophys. Res. Commun.* 147:854-862 (1987), which is hereby incorporated by reference in its entirety), and hence the ability to co-deposit on existing plaques, the sequence of Aβ12-28 was modified by replacing valine for proline in position 18. This renders Aβ12-28P non-fibrillogenic as demonstrated using circular dichroism and Thioflavin-T assays, as well as being non-toxic in cell culture studies. These modifications did not abolish the affinity of Aβ12-28P to apoE. On a competitive inhibition assay, Aβ12-28P bound to apoE, preventing its interaction with full length Aβ immobilized on a solid phase ($IC_{50}$=36.7 nM). The effect of apoE on Aβ fibril formation and toxicity in cell culture was significantly reduced in the presence of Aβ12-28P. The use of Aβ12-28P, synthesized with end-protection and using D-amino acids, allowed extension of its half-life in the serum to 62 min. Aβ12-28P is BBB permeable, making it potentially useful as a CNS agent in vivo. $APP^{K670N/M671L}/PS1^{M146L}$ AD Tg mice treated with Aβ12-28P, demonstrated a significantly lower Aβ load, resembling the situation observed in mice with decreased apoE expression (Bales et al., "Lack of Apolipoprotein E Dramatically Reduces Amyloid β-peptide Deposition," *Nature Gen.* 17:263-264 (1997); Bales et al., "Apolipoprotein E is Essential for Amyloid Deposition in the APPV717F Transgenic Mouse Model of Alzheimer's Disease," *Proc. Natl. Acad. Sci. (USA)* 96:15233-15238 (1999); Holtzman et al., "Expression of Human Apolipoprotein E Reduces Amyloid-beta Deposition in a Mouse Model of Alzheimer's Disease," *J. Clin. Invest.* 103:R15-R21 (1999); Holtzman et al., "Apolipoprotein E Isoform-dependent Amyloid Deposition and Neuritic Degeneration in a Mouse Model of Alzheimer's Disease," *Proc. Natl. Acad. Sci. (USA)* 97:2892-2897 (2000); which are hereby incorporated by reference in their entirety). The initial Aβ plaques in $APP^{K670N/M671L}/PS1^{M146L}$ mice appear at three months of age; whereas, between the fourth and the fifth months of life, Aβ deposition follows an exponential curve where new plaques are actively formed and soluble Aβ co-deposits on existing lesions (Wengenack et al., "Quantitative Histological Analysis of Amyloid Deposition in Alzheimer's Double Transgenic Mouse Brain," *Neurosci.* 101:939-944 (2000), which is hereby incorporated by reference in its entirety). It is shown herein that administration of Aβ12-28P for a period as short as one month resulted in a reduction in Aβ load, and plaque density over two fold compared to untreated age matched Tg animals. Treated mice showed a decreased density of plaques of all sizes, suggesting that blocking the role of apoE as a pathological chaperone of Aβ prevents formation of new plaques as well as growth of already existing lesions. This occurs in an absence of a humoral response since no anti-Aβ antibodies were detected in the sera of treated animals.

Pharmacological targeting of the apoE/Aβ interaction has to take into account the potential role of apoE in the clearance of Aβ from the CNS across the BBB (Shibata et al., "Clearance of Alzheimer's Amyloid-$β_{1-40}$ Peptide from Brain by LDL Receptor-related Protein-1 at the Blood-Brain Barrier," *Journal of Clinical Investigation* 106(12):1489-1499 (2000); Zlokovic "Cerebrovascular Transport of Alzheimer's Amyloid β and Apolipoproteins J and E: Possible Anti-amyloidogenic Role of the Blood-Brain Barrier," *Life Sci.* 59:1483-1497 (1996); which are hereby incorporated by reference in their entirety). ApoE KO mice, and mice expressing human apoE4 on murine apoE KO background, have impaired clearance of synthetic Aβ injected into brain parenchyma, compared to mice expressing human isoform E3 (Ji et al., "Amyloid β40/42 Clearance Across the Blood-brain Barrier Following Intra-ventricular Injections in Wild-type, ApoE Knock-out and Human apoE3 or E4 Expressing Transgenic Mice," *J. Alz. Dis.* 3:23-30 (2001), which is hereby incorporated by reference in its entirety). Therefore, apoE plays a dual role in Aβ clearance and deposition, which is likely dependent on the concentration of CNS Aβ and that of other Aβ binding proteins. Given the opposing roles apoE has on Aβ peptides in the CNS, it is conceivable that blocking apoE/Aβ binding would increase the amyloid burden. However, it appears that the role of apoE as a pathological chaperone outweighs its role in Aβ clearance since $APP^{V717F}$/$apoE^{-/-}$ mice have a decrease in both Aβ load and level (Bales et al., "Lack of Apolipoprotein E Dramatically Reduces Amyloid β-peptide Deposition," *Nature Gen.* 17:263-264 (1997); Bales et al., "Apolipoprotein E is Essential for Amyloid Deposition in the APPV717F Transgenic Mouse Model of Alzheimer's Disease," *Proc. Natl. Acad. Sci. (USA)* 96:15233-15238 (1999); Holtzman et al., "Expression of Human Apolipoprotein E Reduces Amyloid-beta Deposition in a Mouse Model of Alzheimer's Disease," *J. Clin. Invest.* 103:R15-R21 (1999); Holtzman et al., "Apolipoprotein E Isoform-dependent Amyloid Deposition and Neuritic Degeneration in a Mouse Model of Alzheimer's Disease," *Proc. Natl. Acad. Sci. (USA)* 97:2892-2897 (2000); which are hereby incorporated by reference in their entirety). Similarly, the pharmacological blocking of the Aβ/apoE interaction in this study is consistent with the dominance of a pathological chaperone function. Evidence comparing Aβ levels in $APP^{V717F}$ Tg mouse strains crossed to either apoE or apoJ knock out lines suggest that apoJ and apoE can effectively replace each other in their Aβ clearance function (DeMattos et al., "ApoE and Clusterin Cooperatively Suppress Aβ Levels and Deposition. Evidence that apoE Regulates Extracellular Aβ Metabolism in vivo," *Neuron* 41:193-202 (2004), which is hereby incorporated by reference in its entirety). It is only when both apoJ and apoE are knocked out that Aβ amyloid deposition is increased (DeMattos et al., "ApoE and Clusterin Cooperatively Suppress Aβ Levels and Deposition. Evidence that apoE Regulates Extracellular Aβ Metabolism in vivo," *Neuron* 41:193-202 (2004), which is hereby incorporated by reference in its entirety).

AD is a progressive disease for which only palliative treatment is currently available. A number of potential new therapeutic approaches targeting the pathogenesis of AD, and β-amyloidosis in particular, are emerging. The vaccination approach has shown great promise in model animals (Sigurdsson et al., "Immunization with a Nontoxic/Nonfibrillar Amyloid-β Homologous Peptide Reduces Alzheimer's Disease Associated Pathology in Transgenic Mice," *Am. J. Pathol.* 159:439-447 (2001); Schenk et al., "Immunization with Amyloid-beta Attenuates Alzheimer-disease-like Pathology in the PDAPP Mouse," *Nature* 400:173-177 (1999); Morgan et al., "Aβ Peptide Vaccination Prevents Memory Loss in an Animal Model of Alzheimer's Disease," *Nature* 408:982-985 (2001); Weiner et al., "Nasal Administration of Amyloid-β Peptide Decreases Cerebral Amyloid Burden in a Mouse Model of Alzheimer's Disease," *Ann.*

Neurol. 48:567-579 (2000); which are hereby incorporated by reference in their entirety); however, human trials have shown toxicity to be a major problem (Sigurdsson et al., "Immunization for Alzheimer's Disease," *Drug Development Research* 56:135-142 (2002), which is hereby incorporated by reference in its entirety). Targeting the secretase enzymes which are responsible for releasing Aβ from APP has also been a major therapeutic focus. However, these enzymes are involved in several other functions (Doerfler et al., "Presenilin-dependent Gamma-secretase Activity Modulates Thymocyte Development," *Proc. Natl. Acad. Sci.* (*USA*) 98:9312-9317 (2001); Figueroa et al., "Presenilin-dependent Gamma-secretase Activity Modulates Neurite Outgrowth," *Neurobiol. Dis.* 9:49-60 (2002); Hadland et al., "Gamma-secretase Inhibitors Repress Thymocyte Development," *Proc. Natl. Acad. Sci.* (*USA*) 98:7487-7491 (2001); Geling et al., "A Gamma-secretase Inhibitor Blocks Notch Signaling in vivo and Causes a Severe Neurogenic Phenotype in Zebrafish," *EMBO Reports* 3:688-694 (2002); which are hereby incorporated by reference in their entirety), and selective inhibition of Aβ cleavage without associated significant toxicity is a substantial issue. Compared to vaccination (Schenk et al., "Immunization with Amyloid-β Attenuates Alzheimer Disease-like Pathology in the PDAPP Mice," *Nature* 400:173-177 (1999), which is hereby incorporated by reference in its entirety) or γ-secretase inhibitors (Lanz et al., "The Gamma-secretase Inhibitor N-[N-(3,5-difluorophenacetyl)-L-alanyl]-S-phenylglycine t-butyl Ester Reduces A Beta Levels in vivo in Plasma and Cerebrospinal Fluid in Young (Plaque-free) and Aged (Plaque-bearing) Tg2576 Mice," *Journal of Pharmacology and Experimental Therapeutics* 305:864-871 (2003), which is hereby incorporated by reference in its entirety), blocking of pathological chaperones is not associated with the risk of an autoimmune reaction or affecting multiple signaling pathways including Notch-1 and wnt (Geling et al., "A Gamma-secretase Inhibitor Blocks Notch Signaling in vivo and Causes a Severe Neurogenic Phenotype in Zebrafish," *EMBO Reports* 3:688-694 (2002); which is hereby incorporated by reference in its entirety). Animals treated with Aβ12-28P did not produce a humoral response. The data demonstrates that inhibiting the Aβ/apoE interaction over a relatively short period of time can have dramatic effects on amyloid burden, highlighting the importance of apoE in the balance of clearance versus aggregation/deposition of Aβ. Therefore inhibitors of Aβ pathological chaperones may be an alternative approach for the treatment of AD amyloidosis. Results of this study make this concept worthy of further exploration, including biochemical and behavioral characterization of the treatment effect in various AD Tg models co-expressing APP mutation(s) and various forms of the human apoE gene.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of treating Alzheimer's Disease in a subject comprising:
   administering to the subject an agent, wherein the agent
   (1) is a protein comprising the amino acid sequence of SEQ ID NO: 4,
   (2) is non-fibrillogenic, and
   (3) inhibits interaction between amyloid-β peptide and apolipoprotein E, compared to when the agent is absent, to treat Alzheimer's Disease in the subject.

2. The method according to claim 1, wherein the protein is prepared with D-amino acids, an amidated C-terminus, or an acetylated N-terminus.

3. The method according to claim 1, wherein said administering is carried out orally, intradermally, intramuscularly, intraperitoneally, intravenously, subcutaneously, or intranasally.

4. A method of inhibiting accumulation of amyloid-β peptide deposits in a subject's brain comprising:
   administering to the subject an agent, wherein the agent
   (1) is a protein comprising the amino acid sequence of SEQ ID NO: 4,
   (2) is non-fibrillogenic, and
   (3) inhibits interaction between amyloid-β peptide and apolipoprotein E, compared to when the agent is absent, to inhibit accumulation of amyloid-β peptide deposits in the subject's brain.

5. The method according to claim 4, wherein the protein is prepared with D-amino acids, an amidated C-terminus, or an acetylated N-terminus.

6. The method according to claim 4, wherein said administering is carried out orally, intradermally, intramuscularly, intraperitoneally, intravenously, subcutaneously, or intranasally.

* * * * *